United States Patent
Iio et al.

(10) Patent No.: US 8,801,679 B2
(45) Date of Patent: Aug. 12, 2014

(54) MEDICATION ADMINISTERING DEVICE

(75) Inventors: Toshiaki Iio, Ehime (JP); Yukihiro Takabatake, Ehime (JP); Hidenori Watanabe, Ehime (JP); Seiji Kikuchi, Ehime (JP)

(73) Assignee: Panasonic Healthcare Co., Ltd., Ehime (JP)

( * ) Notice: Subject to any disclaimer, the term of this patent is extended or adjusted under 35 U.S.C. 154(b) by 465 days.

(21) Appl. No.: 12/920,699

(22) PCT Filed: Apr. 7, 2009

(86) PCT No.: PCT/JP2009/001608
§ 371 (c)(1),
(2), (4) Date: Sep. 2, 2010

(87) PCT Pub. No.: WO2009/125582
PCT Pub. Date: Oct. 15, 2009

(65) Prior Publication Data
US 2011/0004165 A1 Jan. 6, 2011

(30) Foreign Application Priority Data

Apr. 10, 2008 (JP) ................................ 2008-102934
Apr. 23, 2008 (JP) ................................ 2008-113030

(51) Int. Cl.
*A61M 5/32* (2006.01)
*A61M 5/00* (2006.01)

(52) U.S. Cl.
USPC ........... 604/263; 604/163; 604/192; 604/197; 604/232

(58) Field of Classification Search
USPC .......................... 604/263, 232, 163, 192, 197
See application file for complete search history.

(56) References Cited

U.S. PATENT DOCUMENTS 4,968,299 A 11/1990 Ahlstrand et al.
4,973,318 A * 11/1990 Holm et al. .................... 604/208
(Continued)

FOREIGN PATENT DOCUMENTS

EP 0 829 268 3/1998
JP 64-80371 3/1989
(Continued)

OTHER PUBLICATIONS

International Search Report issued Aug. 4, 2009 in International (PCT) Application No. PCT/JP2009/001608.

*Primary Examiner* — Emily Schmidt
*Assistant Examiner* — Lauren M Peng
(74) *Attorney, Agent, or Firm* — Wenderoth, Lind & Ponack, LLP

(57) ABSTRACT

A medication administering device has mounted thereto a preparation syringe containing a preparation and comprises a substantially cylindrical syringe cover that supports the preparation syringe on the inner peripheral face side, a piston that presses on the rear end of the preparation syringe, and a piston case that surrounds the piston, that guides the outer peripheral face of the syringe cover in the direction of the piston on the substantially cylindrical inner peripheral face side, and that is mounted in a state in which the syringe cover is removable. The medication administering device comprises a syringe holder that guides the outer peripheral face of the preparation syringe in the direction of the piston on the cylindrical inner peripheral face side, and whose outer peripheral face is removably fitted together with the inner peripheral face of the syringe cover. A medication administering device comprises a syringe cover for mounting a preparation syringe to a main body, and has uneven faces of different angles of inclination on the end face of the syringe cover.

17 Claims, 38 Drawing Sheets

(56) References Cited

U.S. PATENT DOCUMENTS

| | | | |
|---|---|---|---|
| 5,514,097 A | 5/1996 | Knauer | |
| 5,725,508 A | 3/1998 | Chanoch et al. | |
| 5,928,205 A | 7/1999 | Marshall | |
| 6,090,082 A * | 7/2000 | King et al. | 604/234 |
| 6,132,395 A | 10/2000 | Landau et al. | |
| 6,447,480 B1 | 9/2002 | Brunel | |
| 6,454,746 B1 | 9/2002 | Bydlon et al. | |
| 6,585,698 B1 * | 7/2003 | Packman et al. | 604/207 |
| 6,638,255 B1 | 10/2003 | Weber | |
| D493,526 S | 7/2004 | Hwang | |
| 7,704,237 B2 | 4/2010 | Fisher et al. | |
| 8,062,252 B2 | 11/2011 | Alheidt et al. | |
| 8,562,582 B2 | 10/2013 | Tuckwell et al. | |
| 2004/0133162 A1 * | 7/2004 | Trocki et al. | 604/131 |
| 2004/0215148 A1 | 10/2004 | Hwang et al. | |
| 2004/0236285 A1 | 11/2004 | Fisher et al. | |
| 2005/0154351 A1 * | 7/2005 | Graf et al. | 604/207 |
| 2006/0189933 A1 | 8/2006 | Alheidt et al. | |
| 2007/0066938 A1 * | 3/2007 | Iio et al. | 604/152 |
| 2007/0142789 A1 | 6/2007 | Fisher et al. | |
| 2008/0015510 A1 | 1/2008 | Sandoz et al. | |
| 2010/0168712 A1 | 7/2010 | Tuckwell et al. | |

FOREIGN PATENT DOCUMENTS

| | | |
|---|---|---|
| JP | 4-312469 | 11/1992 |
| JP | 5-337180 | 12/1993 |
| JP | 8-730 | 1/1996 |
| JP | 10-99434 | 4/1998 |
| JP | 11-76404 | 3/1999 |
| JP | 11-502448 | 3/1999 |
| JP | 2000-237311 | 9/2000 |
| JP | 2001-170176 | 6/2001 |
| JP | 2002-502296 | 1/2002 |
| JP | 2002-526175 | 8/2002 |
| JP | 2002-531227 | 9/2002 |
| JP | 2003-505160 | 2/2003 |
| JP | 2004-535255 | 11/2004 |
| JP | 3686083 | 6/2005 |
| JP | 2005-287676 | 10/2005 |
| JP | 2006-515196 | 5/2006 |
| JP | 2006-271461 | 10/2006 |
| JP | 2007-519503 | 7/2007 |
| JP | 2008-529717 | 8/2008 |
| WO | 2007/140238 | 12/2007 |

* cited by examiner (a)

(b)

(c)

(a)

(b)

(c)

(a)

(b)

(a)

(b)

MEDICATION ADMINISTERING DEVICE

BACKGROUND OF THE INVENTION

I. Technical Field

The present invention relates to a medication administering device to which a preparation syringe containing a preparation is mounted, and which allows a preparation to be administered to a living body and attachment and removal of a medication administering device and a preparation syringe in more detail.

II. Description of the Related Art

Medication administering devices with which a needle is retracted after a living body has been manually punctured and a preparation injected have seen practical applications in the past as medication administering devices for easily administering a preparation to a living body.

For example, Published Japanese Translation No.2002-502296 of the PCT international Publication (published Jan. 22, 2002) discloses a constitution in which a preparation syringe 3 containing a preparation is inserted into a syringe cover 4 as shown in FIG. 1(a), after which the syringe cover 4 is mounted to a medication administering device 1 that includes an administration button (not shown) for pushing out a piston 2 as shown in FIG. 1(b). The syringe cover 4 has a puncture needle mounting portion 4a that allows the mounting of a puncture needle, a fastening tab 4b that mates with a fastening groove 1a in the medication administering device 1 and allows fixing, and a housing 4c into which the preparation syringe 3 can be inserted.

SUMMARY OF INVENTION

However, the following problems were encountered with the conventional medication administering device discussed above.

Specifically, with the medication administering device disclosed in the above publication, after the preparation syringe 3 is inserted into the syringe cover 4, the syringe cover 4 is mounted to the medication administering device 1 so that the fastening tab 4b is fixed in the fastening groove 1a, and a puncture needle for injecting the preparation is attached to the puncture needle mounting portion 4a. The amount of preparation to be injected is then set, and the needle is removed from the body after the skin is punctured and the administration button is pressed to inject the preparation. Accordingly, with the conventional medication administering device above, as shown in FIG. 1(b), when the syringe cover 4 into which the preparation syringe 3 has been inserted is mounted to the medication administering device 1, there is the risk that the preparation syringe 3 will ooze from or fall out of the syringe cover 4. Also, during the above-mentioned mounting, it is necessary to align the position of the piston 2 with the rear end (sealing rubber 3b) of the preparation syringe 3, which is a problem in that the product is harder for the patient to use.

It is an object of the present invention to solve the above-mentioned problems and provide a medication administering device with which the preparation syringe can be attached and detached simply and reliably, and both reliability and ease of use can be improved.

The medication administering device pertaining to the present invention is a medication administering device to which a preparation syringe containing a preparation is mounted, and which administers a preparation to a living body, said device comprising a substantially cylindrical syringe cover, a piston, and a piston case. The substantially cylindrical syringe cover supports the preparation syringe on the inner peripheral face side. The piston presses on the rear end of the preparation syringe. The piston case surrounds the piston, guides the outer peripheral face of the syringe cover in the direction of the piston on the substantially cylindrical inner peripheral face side, and is mounted in a state in which the syringe cover is removable.

Here, with a medication administering device in which a substantially cylindrical syringe cover is mounted so that the rear end portion of a preparation syringe will be disposed in close proximity to the piston in a state in which the preparation syringe has been inserted into the syringe cover, the piston case surrounds the piston, and the syringe cover is guided in the direction of the piston along the cylindrical inner peripheral face.

Consequently, after the preparation syringe has been mounted to the syringe cover, the syringe cover can be inserted along the inner peripheral face of the piston case until it is in close proximity to the piston. This stabilizes the mounting of the syringe cover to the piston case, and prevents the occurrence of problems such as the preparation syringe falling out of the syringe cover, so the syringe cover can be placed more securely inside the device.

The medication administering device pertaining to the present invention is one with which a preparation syringe containing a preparation is mounted thereto, and which administers a preparation to a living body, and comprises a syringe cover, a piston, and a syringe holder. The syringe cover is a substantially cylindrical member that supports a preparation syringe on the inner peripheral face side. The piston presses on the rear end of the preparation syringe. The syringe holder surrounds the piston at a specific position, guides the outer peripheral face of the preparation syringe in the direction of the piston on the cylindrical inner peripheral face side, and has an outer peripheral face that is removably fitted together with the inner peripheral face of the syringe cover.

As a result of this constitution, the user can easily mount the preparation syringe to this medication administering device, and there is no need for alignment of the piston and the preparation syringe. Therefore, the user has to do less work.

The medication administering device pertaining to the present invention is a medication administering device is a medication administering device to which a preparation syringe containing a preparation is mounted, and which administers a preparation to a living body, said device comprising a main body, an inner case that forms the main body, a syringe holder, a spring, and a syringe cover. The syringe holder is installed inside the inner case and supports the preparation syringe. The spring biases the syringe holder in one direction. The syringe cover allows a needle for administering the preparation to be attached to its distal end portion, and surrounds the preparation syringe, has uneven faces of different angles of inclination on its end face, and mounts the preparation syringe to the main body in conjunction with syringe holder and/or the inner case.

With this constitution, a medication administering device can be provided with which the syringe cover is easy to mount and more difficult to remove, that is, easy to mount and resistant to coming loose, so ease of use and reliability are excellent.

The medication administering device pertaining to the present invention is a medication administering device is a medication administering device to which a preparation syringe containing a preparation is mounted, and which administers a preparation to a living body, said device comprising a main body, a cylindrical syringe holder, a cylindrical syringe cover, and inner case, and a distal end cap. The main body administers the preparation. The cylindrical syringe holder is provided to the main body, and the preparation syringe is inserted therein from the rear end side. The cylindrical syringe cover supports the preparation syringe on the inner peripheral face side, and the preparation syringe is inserted therein from the distal end side. The inner case guides the syringe cover while being removably fitted together with the syringe cover. The distal end cap guides the main body while being removably fitted together with the main body, and moves in conjunction with the syringe cover during attachment to the main body.

With this constitution, the distal end cap moves in conjunction with the syringe cover when the distal end cap is attached to the main body, so even if the syringe cover is not properly attached, the syringe cover can still be guided to the proper mounting position. As a result, the user can easily and reliably mount the syringe cover or the distal end cap to this medication administering device.

The medication administering device pertaining to the present invention is a medication administering device to which a preparation syringe containing a preparation is mounted, and which administers a preparation to a living body, said device comprising a main body, a cylindrical syringe cover, and a distal end cap. The syringe cover has a removably attached a needle portion that includes a needle that pierces into the living body in order to administer the preparation and that injects the preparation. The distal end cap covers all or part of the syringe cover, is removably fitted together with the main body, and has a distal end opening through which the needle slides. Also, the distal end cap is such that when a cap of the needle portion is removed through the distal end opening, this cap is moved to the distal end side, and the cap can be removed from the needle portion.

With this constitution, when a finger is stuck into the distal end opening of the distal end cap and the protective cap or the like of the needle portion is removed, the protective cap is moved toward the distal end side and can be removed. As a result, the user can easily remove the needle cap or protective cap of the needle portion from this medication administering device.

DETAILED DESCRIPTION OF THE PREFERRED EMBODIMENTS (Embodiment 1)

A medication administering device 11 pertaining to an embodiment of the present invention will now be described through reference to FIGS. 2 to 9.

Figure 1:
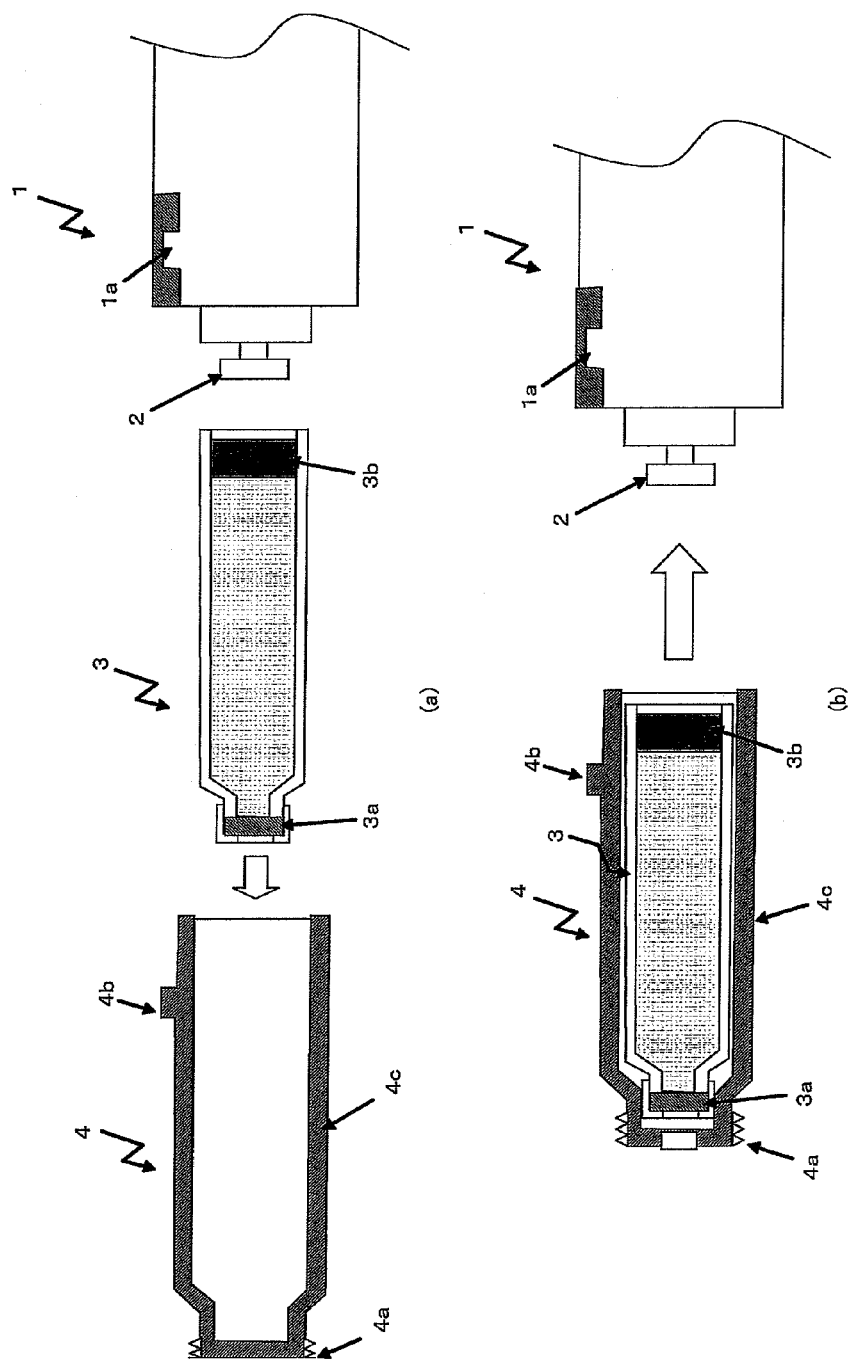
FIG. 1(a) is a diagram of the constituent parts of a conventional medication administering device.
FIG. 1(b) is a diagram of the preparation syringe mounting in a conventional medication administering device.
Figure 2:
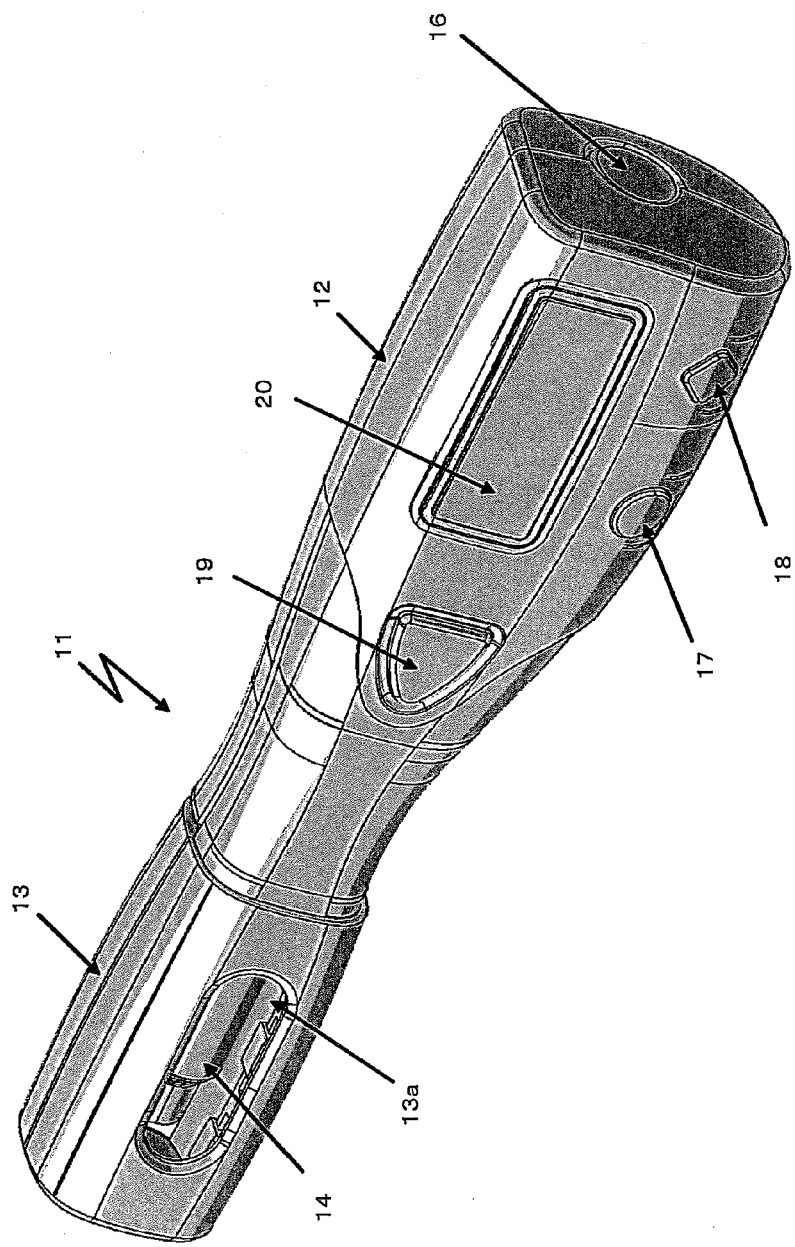
FIG. 2 is an overall oblique view of the medication administering device in Embodiment 1 of the present invention.

As shown in FIG. 2, the medication administering device 11 in this embodiment is covered by a housing 12, which is the outer covering of the device main body. Power to the medication administering device 11 can be switched on and off with a power button 16, and air inside the preparation syringe can be vented with an air vent button 17. The medication administering device 11 also has a completion button 18 that allows the flow to move on to the next step upon completion of a required operation, such as after air venting or the confirmation of various displays, a medication administering button 19 that is pressed at the time of medication administration after completion of preparation for administering the medication, and an LCD 20 that displays various kinds of necessary information, such as the remaining battery charge or the air venting operation. The medication administering device 11 also has a distal end cap 13 that can be attached to and detached from one end of the housing 12. The distal end cap 13 is attached or removed as needed in the attachment and removal of the puncture needle that injects the medication solution or the preparation syringe, and has a check window 13a used to check the interior. Therefore, the type of preparation syringe, whether or not there is a preparation syringe, the amount of preparation, and so forth can be checked through a syringe cover 14 formed from a transparent material.

Figure 3:
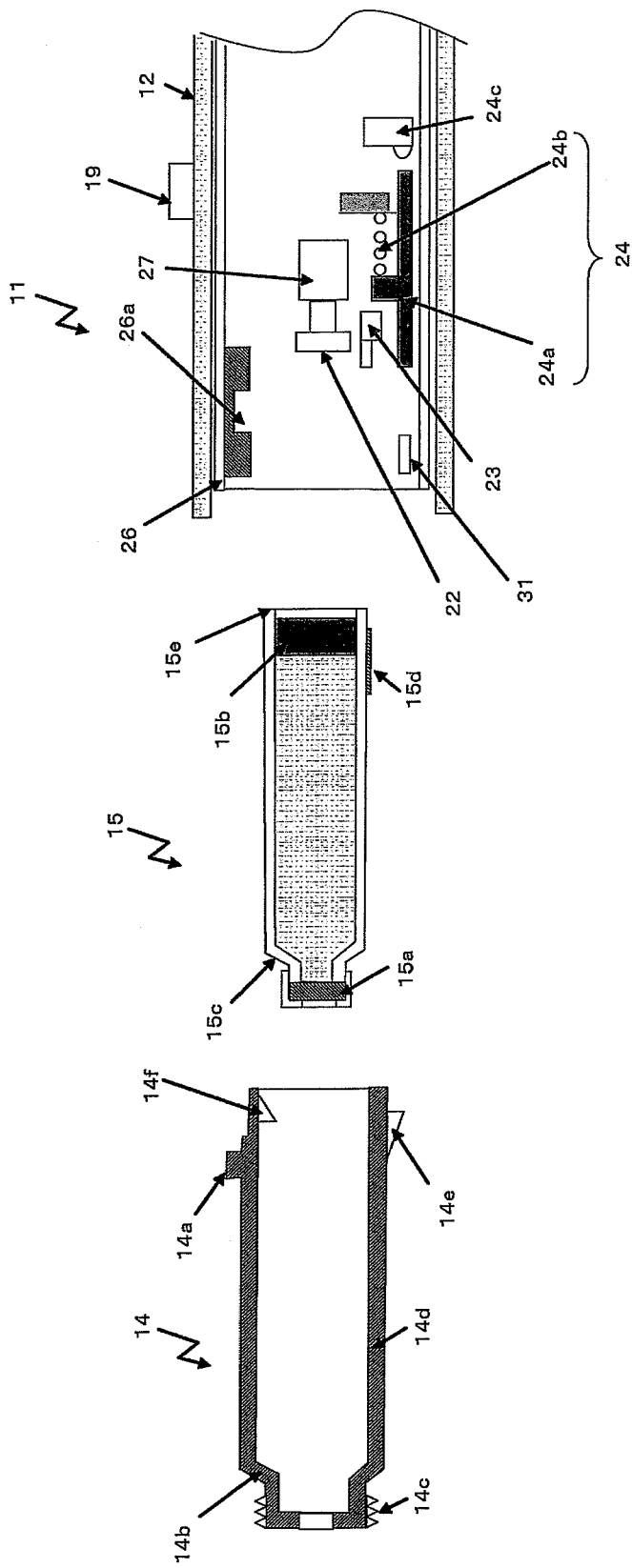
FIG. 3 is an internal cross section of the constituent parts of the medication administering device in FIG. 2.

As shown in FIG. 3, the medication administering device 11 further comprises the syringe cover 14 inserted inside the housing 12, a preparation syringe 15, and a piston case 26.

(Syringe Cover 14)

As shown in FIG. 3, the syringe cover 14 comprises a fastening tab 14a, a syringe contact-use inclined part 14b, a puncture needle mounting portion 14c, a housing 14d, a detection tab 14e, and a syringe mounting prong 14f.

The fastening tab 14a mates with a fastening groove 26a formed on the inner peripheral face side of the piston case 26 provided inside the housing 12.

The syringe contact-use inclined part 14b is formed so as to come into precise contact with a syringe cover contact-use inclined part 15c provided to one end of the preparation syringe 15 that contains the preparation.

The puncture needle mounting portion 14c allows the mounting of a puncture needle for injecting a medication solution into the skin.

The housing 14d is substantially cylindrical member inside of which the preparation syringe 15 can be stowed.

The detection tab 14e is provided to press on one end of a syringe cover detecting lever 24a constituted on the inside of the housing 12 of the medication administering device 11.

The syringe mounting prong 14f supports a syringe end face 15e of the preparation syringe 15 (discussed below), and prevents the preparation syringe 15 from falling out of the syringe cover 14.

(Preparation Syringe 15)

The preparation syringe 15 has rubber seals 15a and 15b, the syringe cover contact-use inclined part 15c, an ID (identification piece) 15d, and the syringe end face 15e.

The rubber seals 15a and 15b are provided to seal the ends of the preparation syringe 15 and hold in the preparation.

The syringe cover contact-use inclined part 15c comes into precise contact with the syringe contact-use inclined part 14b formed at one end of the syringe cover 14.

The ID (identification piece) 15d is used to identify the preparation syringe 15, and the user can identify the type of preparation in the preparation syringe 15 and other such information by reading the ID 15d. A tag, bar code, or the like may be used instead of this ID.

The syringe end face 15e is supported by the syringe mounting prong 14f provided to the syringe cover 14 when the preparation syringe 15 is inserted into the syringe cover 14.

(Piston Case 26 and its Internal Configuration)

The piston case 26 is a substantially cylindrical member provided along the inner wall face of the housing 12, and is provided with a medication administering button 19 on the outer peripheral face side, and on the inner peripheral face side with a piston 22, a syringe detection switch 23, a syringe cover detector 24, a piston drive motor 27, and a syringe identifier 31.

The medication administering button 19 is provided to a side face of the medication administering device 11, and is pressed when the preparation is to be administered.

The piston 22 moves forward while in contact with the rubber seal 15b provided to the rear end of the preparation syringe 15, and pushes out the preparation toward the administration side.

The syringe detection switch 23 is pushed down by the syringe end face 15e of the preparation syringe 15 when the syringe cover 14 to which the preparation syringe 15 is mounted is inserted into the piston case 26. Consequently, it can be detected from the operation of the switch that the preparation syringe 15 has been mounted in the syringe cover 14.

The syringe cover detector 24 has a syringe cover detecting lever 24a, a syringe cover detecting lever spring 24b, and a syringe cover detection switch 24c. When the syringe cover 14 is inserted into the piston case 26, the syringe cover detection switch 24c moves against the spring force of the syringe cover detecting lever spring 24b and pushes down the syringe cover detection switch 24c. Consequently, it can be detected that the syringe cover 14 has been mounted in the piston case 26.

The piston drive motor 27 rotates in the desired direction to move the piston 22 back and forth in the direction of preparation administration. The syringe identifier 31 reads information about the ID 15d of the preparation syringe 15 to detect that the syringe cover 14 has been mounted and determine the types and others of preparation syringe 15.

<Method for Operating the Medication Administering Device 11>

The method for operating the medication administering device 11 in this embodiment will now be described through reference to FIGS. 4 to 9.

Figure 4:
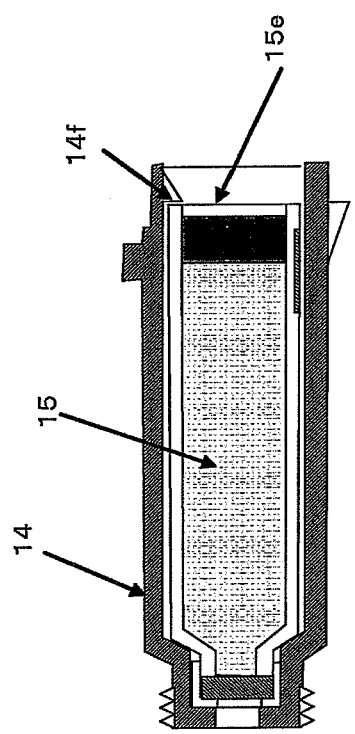
FIG. 4 is an internal cross section of a state in which the preparation syringe has been mounted in the syringe cover in the medication administering device in FIG. 2.
Figure 4:
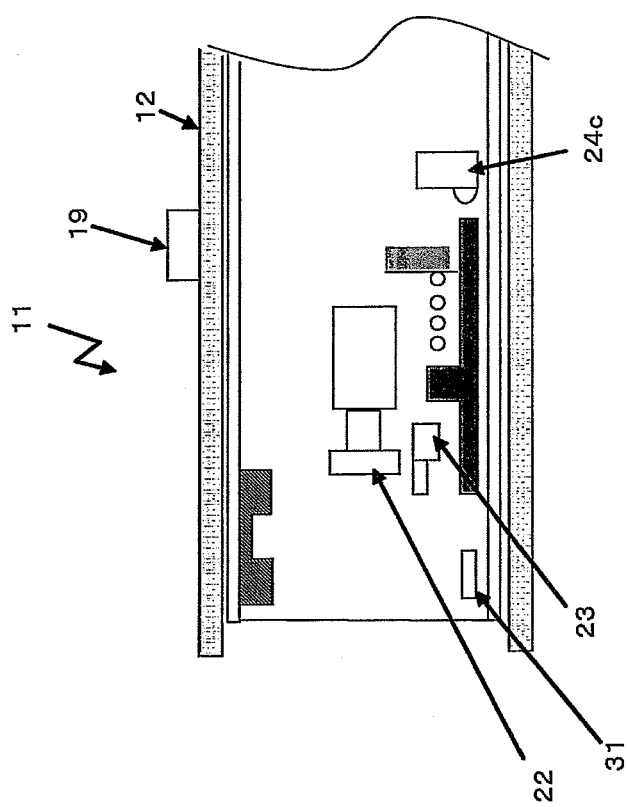

First, as shown in FIG. 4, the preparation syringe 15 is inserted on the inner peripheral face side of the syringe cover 14, which is substantially cylindrical in shape. At this point the syringe mounting prong 14f supports the syringe end face 15e at the rear end of the preparation syringe 15. Consequently, even if the syringe cover 14 is tilted, the preparation syringe 15 can be held inside the syringe cover 14.

Figure 5:
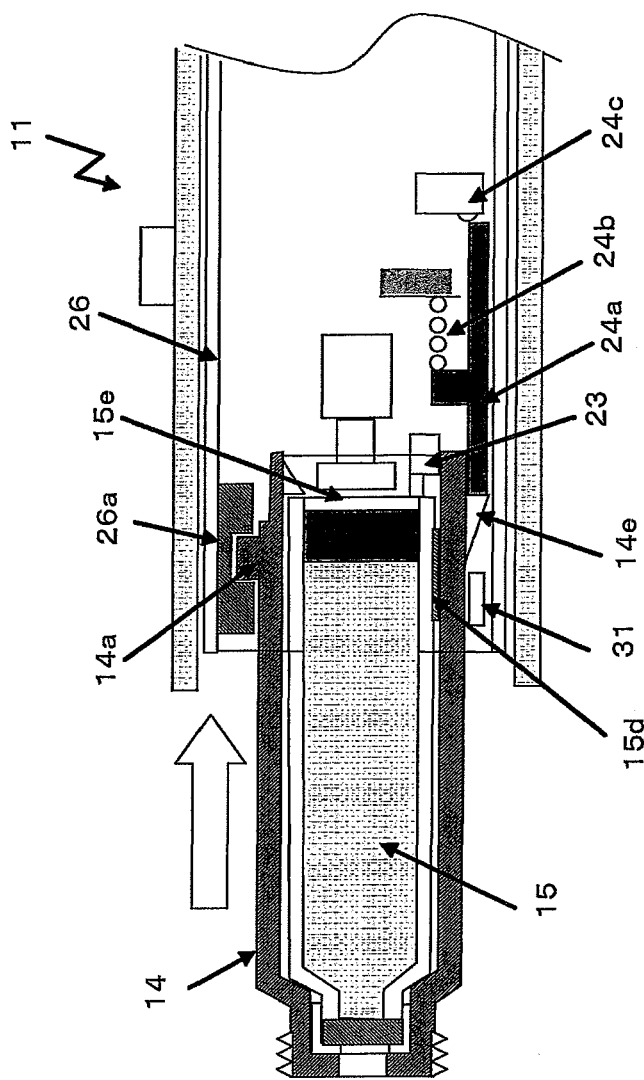
FIG. 5 is an internal cross section of a state in which the syringe cover has been mounted to the main body in the medication administering device in FIG. 2.

After this, as shown in FIG. 5, the syringe cover 14 supporting the preparation syringe 15 is mounted inside the piston case 26. The fastening tab 14a and the fastening groove 26a fit together at this point, so that the syringe cover 14 is fixed inside the piston case 26.

In the course of inserting the syringe cover 14 here, the syringe end face 15e of the preparation syringe 15 pushes down the syringe detection switch 23. Consequently, the medication administering device 11 detects from the operation of the switch that the preparation syringe 15 has been mounted.

The ID 15d of the preparation syringe 15 is then read by the syringe identifier 31, and the medication administering device 11 determines whether or not the inserted preparation syringe 15 contains the desired preparation.

The detection tab 14e pushes down the syringe cover detecting lever 24a, which operates the syringe cover detection switch 24c. Consequently, the medication administering device 11 can detect that the syringe cover 14 has been mounted. The syringe cover detecting lever spring 24b at this point is held in a compressed state.

Figure 6:
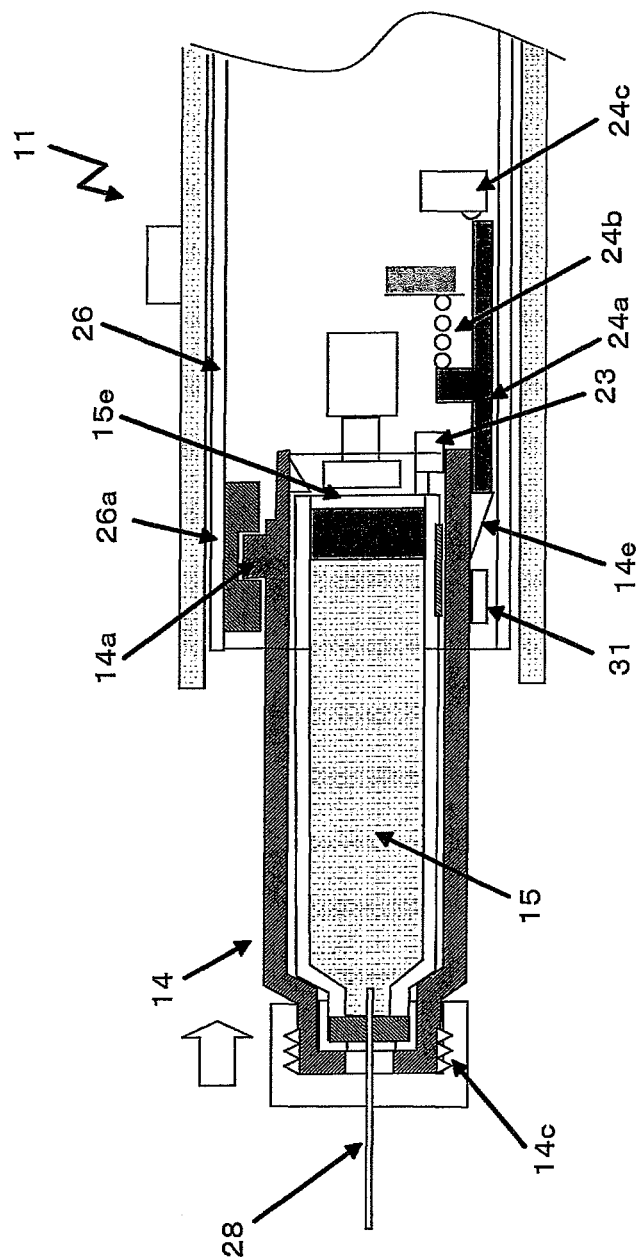
FIG. 6 is an internal cross section of a state in which the a puncture needle has been mounted in the medication administering device in FIG. 2.

Then, as shown in FIG. 6, a puncture needle 28 that is stuck into the body of a person, etc., and injects a medication solution from the puncture tip is placed in the puncture needle mounting portion 14c at the distal end of the preparation syringe 15.

Figure 7:
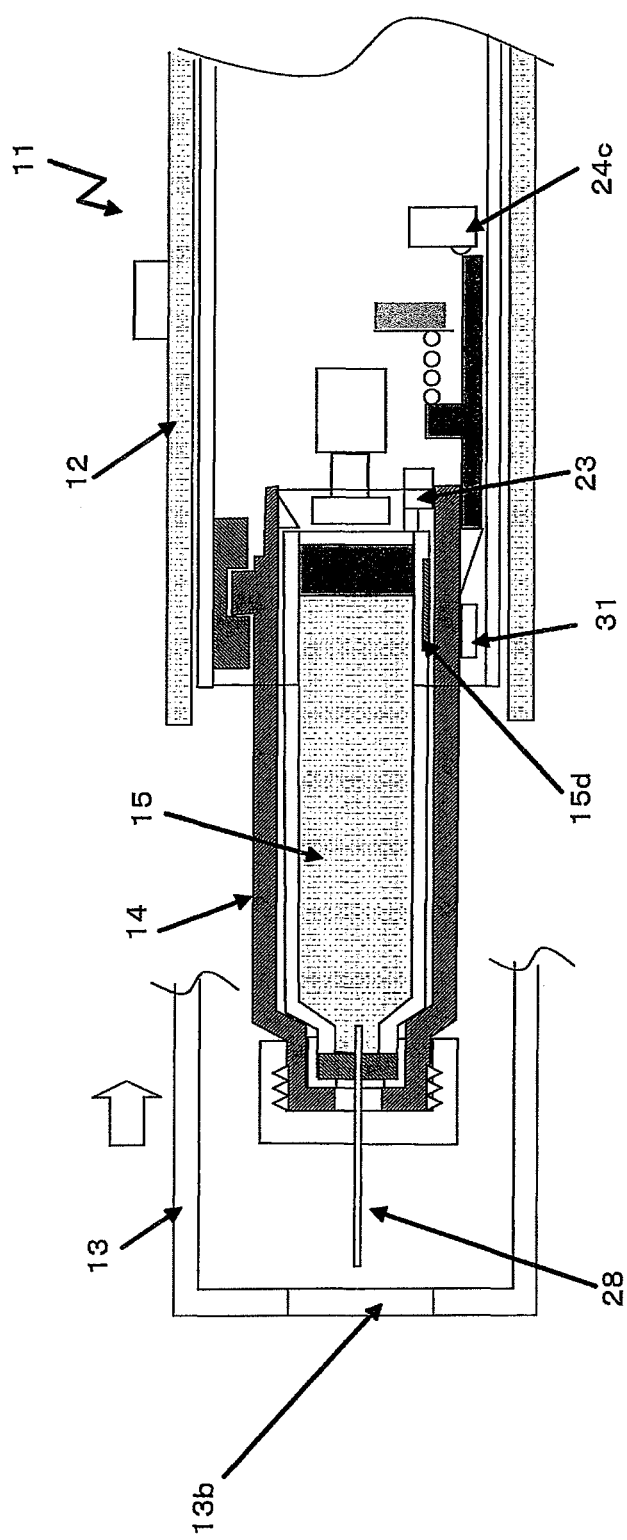
FIG. 7 is an internal cross section of a state in which the distal end cap has been mounted in the medication administering device in FIG. 2.

Then, as shown in FIG. 7, the distal end cap 13 that is in contact with the skin of a person, etc., is mounted to the distal end of the housing 12 on the medication administration side. An opening 13b through which the puncture needle 28 passes is formed in the center of the distal end cap 13.

After the pre-use preparation has been performed as discussed above by going through the steps shown in FIGS. 4 to 7, the power button 16 (see FIG. 2) is pressed to supply power to the medication administering device 11. At this point the medication administering device 11 checks the status of the syringe detection switch 23 and the syringe cover detection switch 24c, and checks whether or not the preparation syringe 15 or the syringe cover 14 has been mounted. The syringe identifier 31 reads information about the ID 15d of the preparation syringe 15, and it is confirmed whether or not the correct preparation syringe 15 has been mounted. On the condition that all of these checks have been completed, the air vent button 17 is then pressed in the next operation (see FIG. 2).

Next, when the air vent button 17 is pressed, a piston case drive motor (not shown) slides the entire piston case 26 by approximately 10 mm to the left with respect to the housing 12. The piston drive motor 27 is then actuated, and the piston 22 moves by a specific amount to the left to vent air. At this point, the rubber seal 15b is pushed in in the puncture direction (to the left in the drawings), and the air inside the preparation syringe 15 is discharged from the puncture needle 28. After this, the piston case drive motor is reversed, and the entire piston case 26 slides 10 mm in the opposite direction from the puncture direction (to the right in the drawings) with respect to the housing 12, thus returning to its original position.

Figure 8:
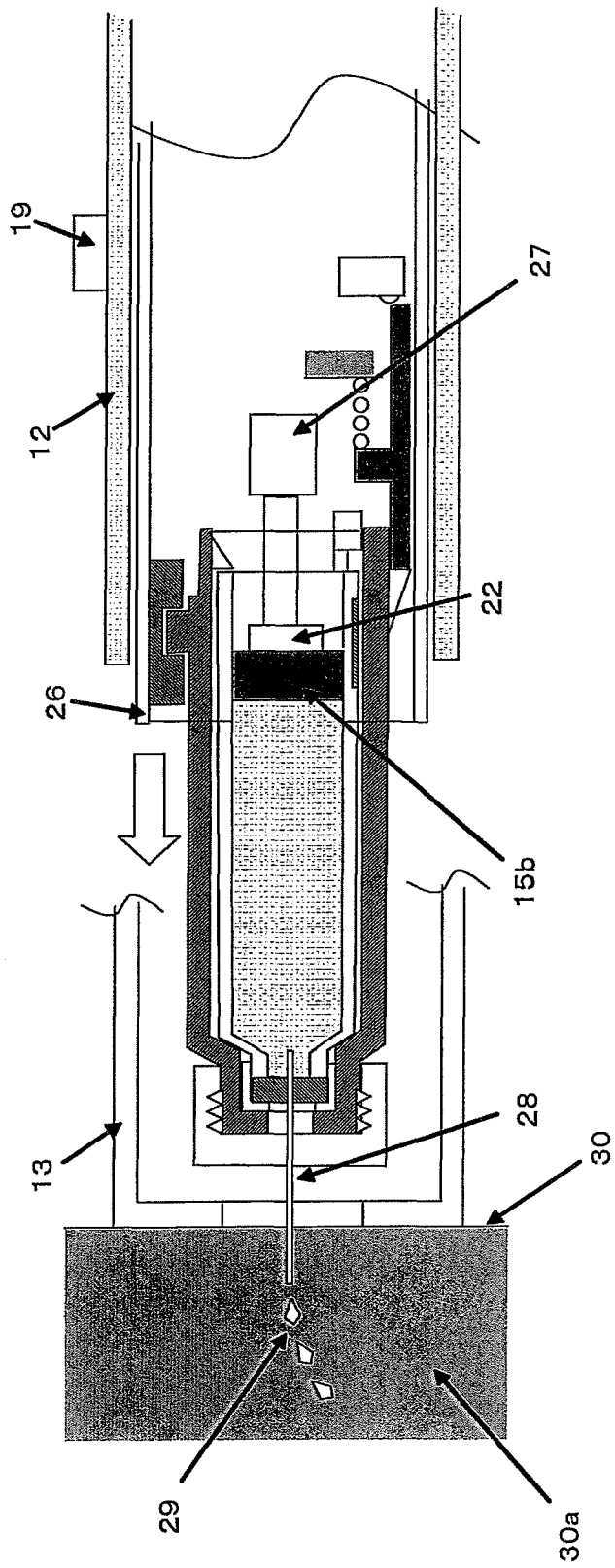
FIG. 8 is an internal cross section of the administration state of the medication administering device in FIG. 2.

Next, as shown in FIG. 8, the flow moves to a step of administering the preparation, but the basic operation is the same as that of the air venting discussed above.

That is, when the distal end cap 13 is brought into contact with the skin 30 and the medication administering button 19 is pressed, the piston case drive motor (not shown) slides the entire piston case 26 by approximately 10 mm in the puncture direction (to the left in the drawings) with respect to the housing 12. The distal end of the puncture needle 28 is exposed from the distal end cap 13 and reaches the subcutaneous layer 30a from the skin 30.

Next, the piston drive motor 27 is actuated, the piston 22 moves a specific amount for preparation injection in the puncture direction (to the left in the drawings), and the rubber seal 15b is pushed in in the puncture direction (to the left in the drawings). As a result, the preparation 29 inside the preparation syringe 15 is injected from the puncture needle 28 to the subcutaneous layer 30a. After this, the piston case drive motor is reversed, and the entire piston case 26 slides approximately 10 mm in the opposite direction from the puncture direction (to the right in the drawings) with respect to the housing 12, thus returning to its original position. Therefore, the puncture needle 28 is pulled out of the skin 30 or subcutaneous layer 30a, and put back inside the distal end cap 13.

Figure 9:
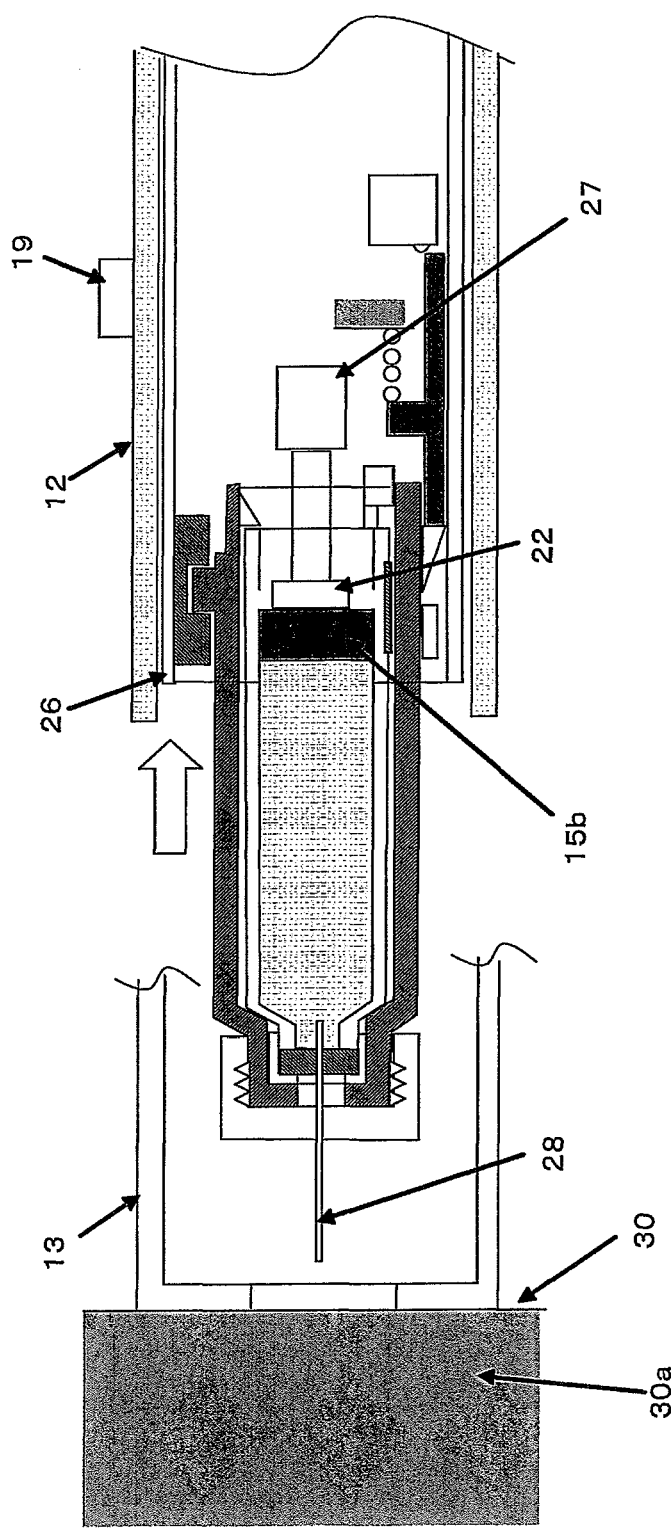
FIG. 9 is an internal cross section of the state after administration with the medication administering device in FIG. 2.

Next, as shown in FIG. 9, after the preparation has been administered, the piston case 26 is retracted with respect to the housing 12, and the puncture needle 28 is removed from the skin 30.

In this embodiment, as discussed above, the medication administering device 11 in which the preparation syringe 15 containing the preparation is mounted inside the syringe cover 14, and a preparation can be administered to a living body or the like, comprises the syringe cover 14 that supports the preparation syringe 15, and the piston case 26 to which the syringe cover 14 is removably mounted.

Consequently, when the preparation syringe 15 is mounted to the piston case 26, the syringe cover 14 can be mounted easily, safely, and reliably, without worrying about the orientation during attachment or about whether the preparation syringe 15 will fall out.

Also, in this embodiment, the syringe detection switch 23 is provided inside the piston case 26. Consequently, whether or not the preparation syringe 15 has been properly mounted can be easily detected.

Also, the syringe identifier 31 is provided inside the piston case 26. Consequently, the ID 15d of the preparation syringe 15 can be read, and whether or to the correct preparation syringe 15 has been mounted can be detected.

Furthermore, the syringe cover detector 24 is provided inside the piston case 26. Consequently, whether or not the syringe cover 14 has been mounted can be easily detected.

Thus, because of these detection functions, a safe medication administering device 11 can be provided which will not be accidentally operated at an unintended place.

(Embodiment 2)

The configuration of a syringe cover 114 used in a medication administering device pertaining to another embodiment of the present invention will be described below through reference to FIGS. 10 to 13. Those components that are shared with the above-mentioned Embodiment 1 will be numbered the same and not described again.

Figure 10:
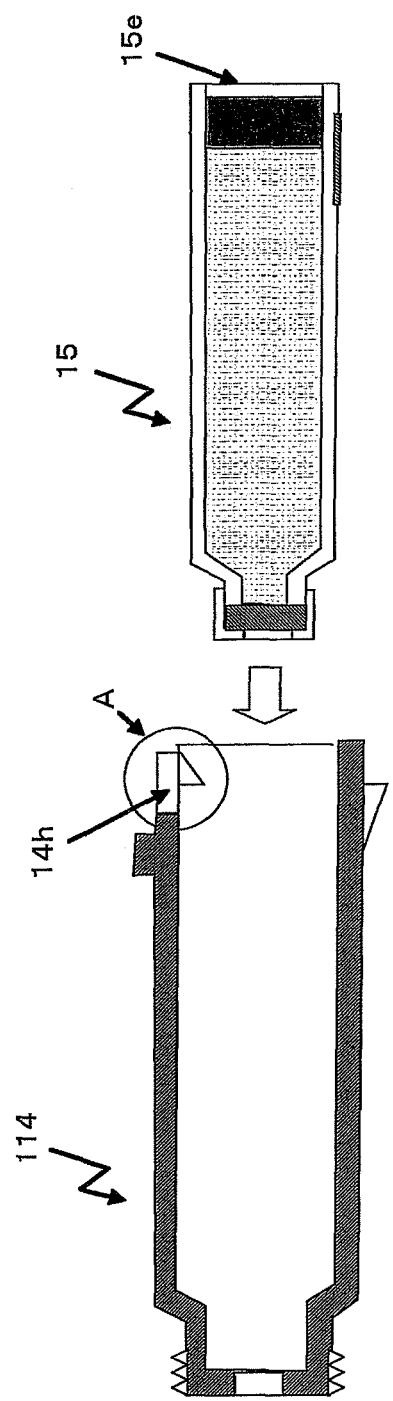
FIG. 10 is an internal cross section of the syringe cover and the preparation syringe of a medication administering device pertaining to Embodiment 2 of the present invention.

With the syringe cover 114 in this embodiment, as shown in FIG. 10, etc., what is different from the syringe cover 14 in Embodiment 1 is the use of a syringe mounting arm 14h as the member that supports the rear end of the preparation syringe 15.

Figure 11:
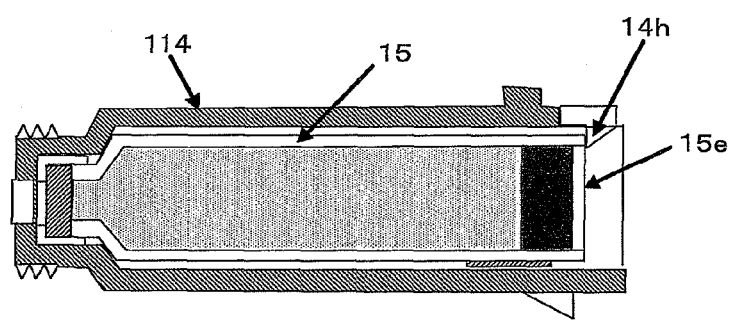
FIG. 11 is an internal cross section of a state in which the preparation syringe has been mounted in the syringe cover in the medication administering device in FIG. 10.

More precisely, as shown in FIG. 11, the syringe cover 114 in this embodiment has a rotatable syringe mounting arm 14h for supporting the syringe end face 15e of the preparation syringe 15 and preventing it from falling out.

Consequently, after the syringe cover 114 to which the preparation syringe 15 has been mounted is placed inside the above-mentioned piston case 26, the used preparation syringe 15 can be simply taken out after the preparation has been administered from the distal end of the puncture needle 28.

Figure 12:
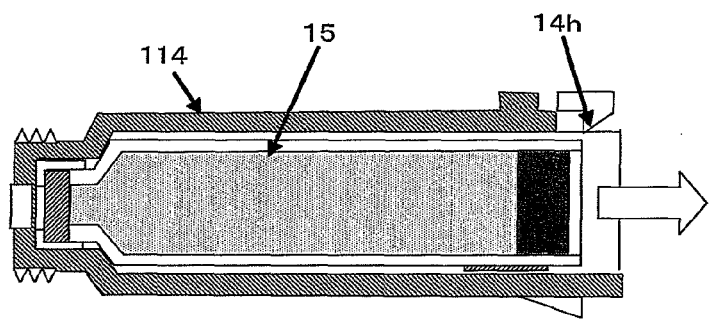
FIG. 12 is an internal cross section of a state in which the preparation syringe has been removed from the syringe cover in the medication administering device in FIG. 10.

As shown in FIG. 12, when the preparation syringe 15 inserted in the syringe cover 114 is taken out, the distal end of the syringe mounting arm 14h, which was supporting the syringe end face 15e of the preparation syringe 15, is retracted. Consequently, the preparation syringe 15 can be easily taken out of the syringe cover 14 merely by rotating the syringe mounting arm 14h.

Figure 13:
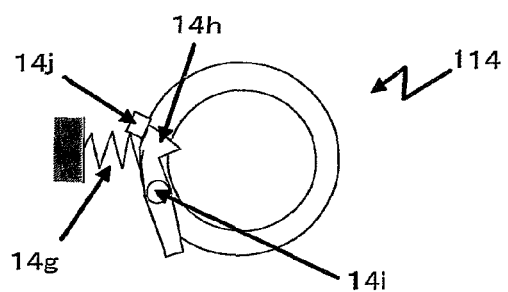
FIG. 13 is a detail view of portion A in FIG. 10, illustrating the configuration as seen from an end face of the syringe cover included in the medication administering device.

As shown in FIG. 13, the syringe mounting arm 14h is supported in a state of being rotatable around a support shaft 14i, and is biased in the clockwise direction (the right rotation direction) by a mounting arm spring 14g. A stopper 14j is formed integrally with the syringe mounting arm 14h, and comes into contact with the inner peripheral face of the syringe cover 114.

Consequently, when the syringe mounting arm 14h is rotated counter-clockwise, the distal end of the syringe mounting arm 14h can be retracted from the front of the syringe end face 15e. Thus, the preparation syringe 15 can be simply taken out of the syringe cover 114.

(Embodiment 3)

A medication administering device 111 pertaining to another embodiment of the present invention will be described below through reference to FIGS. 2 and 14 to 20. Those components that are shared with the above-mentioned Embodiments 1 and 2 will be numbered the same and not described again.

The medication administering device 111 in this embodiment mainly differs from the medication administering device 11 in Embodiment 1, which had not syringe holder, in that a syringe holder 21 is disposed inside the housing 12.

As shown in FIG. 2, the medication administering device 111 in this embodiment is covered by the housing 12, which is the outer covering of the device main body. Power to the medication administering device 111 can be switched on and off with the power button 16, and air inside the preparation syringe 15 (see FIG. 14) can be vented with the air vent button 17. The medication administering device 111 also has a completion button 18 that allows the flow to move on to the next step upon completion of a required operation, such as after air venting or the confirmation of various displays, a medication administering button 19 that is pressed at the time of medication administration after completion of preparation for administering the medication, and an LCD 20 that displays various kinds of necessary information, such as the remaining battery charge or the air venting operation. The medication administering device 111 also has a distal end cap 13 that can be attached to and detached from one end of the housing 12 as needed during attachment and removal of the puncture needle that injects a medication solution or the preparation syringe 15. The distal end cap 13 is provided with a check window 13a, and the type of preparation syringe, whether or not there is a preparation syringe, the amount of preparation, and so forth can be checked through the transparent syringe cover 14.

Figure 14:
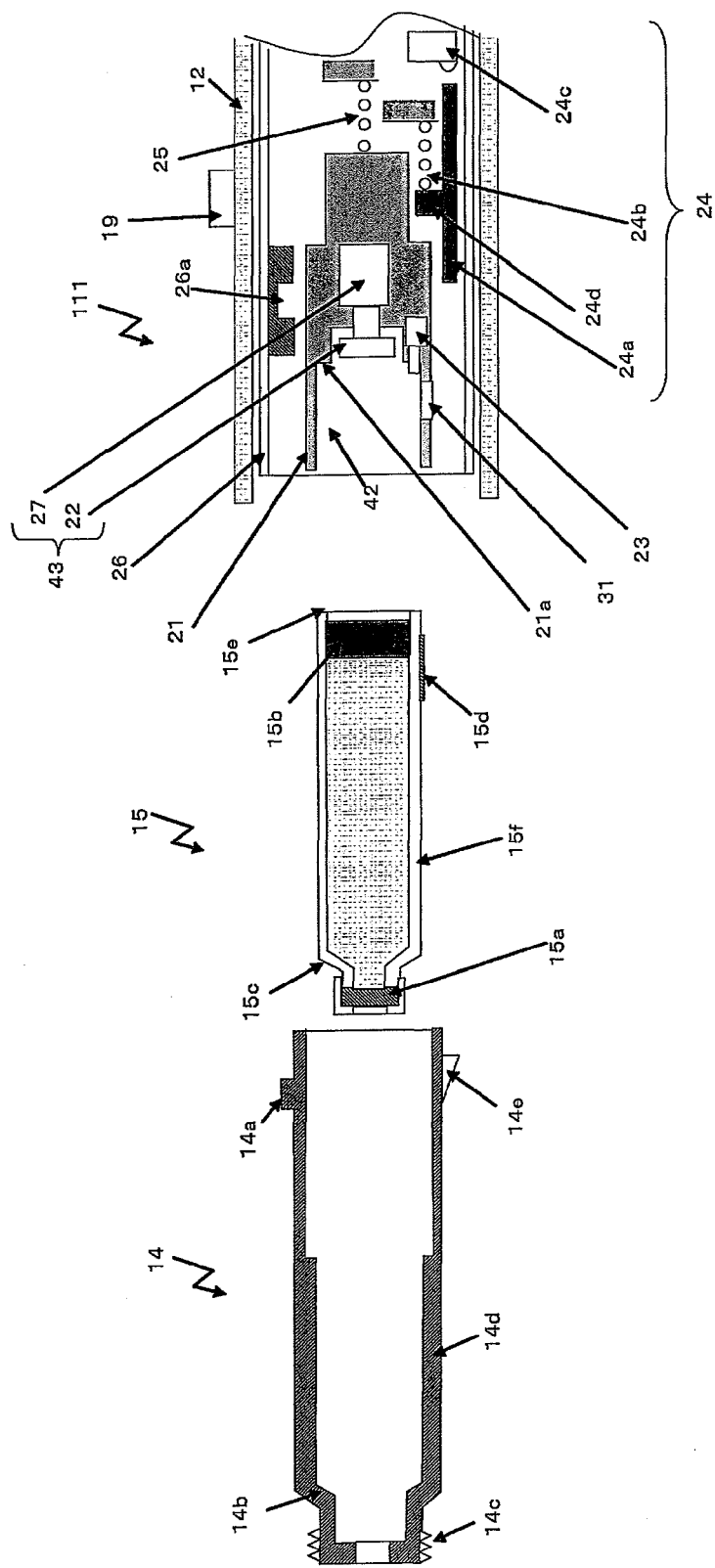
FIG. 14 is an internal cross section of the constituent parts of the medication administering device pertaining to Embodiment 3 of the present invention.

As shown in FIG. 14, the medication administering device 111 further comprises the syringe cover 14 inserted inside the housing 12, the piston case 26, the syringe holder 21, a syringe holder spring (biasing member) 25, and the syringe cover detector 24. The preparation syringe 15 containing a preparation is mounted in the drug administration device 111.

The syringe cover 14 is removably mounted to the piston case 26 and the syringe holder 21, and as shown in FIG. 14, comprises the fastening tab 14a, the syringe contact-use inclined part 14b, the puncture needle mounting portion 14c, the housing 14d, and the detection tab 14e.

The fastening tab 14a is formed so as to protrude up from the outer peripheral face of the syringe cover 14, and is disposed on the rear end side of the syringe cover 14. The fastening tab 14a mates with the fastening groove 26a provided to the piston case 26 provided, in a state in which the syringe cover 14 has been mounted to the device main body.

The syringe contact-use inclined part 14b is formed so as to come into precise contact with the syringe cover contact-use inclined part 15c provided on the distal end side of the preparation syringe 15 when the syringe cover 14 has surrounded the preparation syringe 15.

The puncture needle mounting portion 14c is a portion to which the puncture needle 28 used for injecting a medication solution into a living body (see FIG. 17) is mounted.

The housing 14d is a substantially cylindrical portion that allows the preparation syringe 15 to be stowed inside the syringe cover 14.

The detection tab 14e is provided in order to press one end of the syringe cover detecting lever 24a, which is provided inside the piston case 26, in the rear end direction when the syringe cover 14 has been mounted to the device main body.

The preparation syringe 15 is a member that supports the preparation 29 in its interior, and has a container 15f, the rubber seals 15a and 15b, the syringe cover contact-use inclined part 15c, the ID (identification piece) 15d, and the syringe end face 15e.

The container 15f is a member that is cylindrical in shape, and may be constituted, for example, by a material such as glass or plastic that is not deformed by the pressure of the preparation 29.

The rubber seal 15a seals the distal end side of the container 15f. The rubber seal 15b is a member that is cylindrical in shape, whose peripheral face comes into contact with the inner peripheral face of the container 15f, and which seals the rear end side of the preparation syringe 15. The rubber seal 15b can also be displaced while sliding along the inner peripheral face of the container 15f, that is, while the peripheral face of the rubber seal 15b slides along the inner peripheral face of the container 15f, under an external force. Consequently, the preparation 29 inside the container 15f can be held and preserved while it is possible to exert pressure on the preparation 29 when the rubber seal 15b is pressed by the piston 22 (discussed below).

As discussed above, the syringe cover contact-use inclined part 15c comes into precise contact with the syringe contact-use inclined part 14b formed at one end of the syringe cover 14, in a state in which the preparation syringe 15 is supported by the syringe cover.

The ID (identification piece) 15d is used to identify the preparation syringe 15, and the syringe identifier 31 (discussed below) can identify the type of preparation 29 in the preparation syringe 15 and other such information by reading the ID 15d. A tag, bar code, or the like may be used instead of this ID.

The syringe end face 15e hits and presses on a syringe receiving face 21a when the preparation syringe 15 is mounted inside the syringe holder 21.

The piston case 26 is a cylindrical member provided on the inner peripheral face side of the housing 12, and the fastening groove 26a is formed on the inner peripheral face side thereof. This fastening groove 26a, as discussed above, is formed so as to mate with the fastening tab 14a formed on the outer peripheral face of the syringe cover 14.

The syringe cover detector 24 is used to detect the mounting of the syringe cover 14, and is disposed on the inner peripheral face side of the piston case 26. The syringe cover detector 24 has the syringe cover detecting lever 24a, the syringe cover detecting lever spring 24b, and the syringe cover detection switch 24c.

The syringe cover detecting lever 24a is provided at a position where one end comes into contact with the detection tab 14e provided to the syringe cover 14 when the syringe cover 14 has been mounted to the device main body. Also, the syringe cover detecting lever 24a includes a protrusion 24d formed so as to protrude integrally from a flat member that comes into contact with the detection tab 14e. One end of the syringe cover detecting lever spring 24b is linked to a face of the protrusion 24d on the rear end side of the device, while the other end is fixed to a fixed wall inside the piston case 26. That is, the syringe cover detecting lever spring 24b biases the syringe cover detecting lever 24a toward the distal end from the rear end of the device, which limits the unmounted position of the syringe cover detecting lever 24a. The "unmounted position" here refers to the position in a state in which the syringe cover 14 has yet to be mounted. The syringe cover detection switch 24c is used to detect this mounting when the syringe cover 14 has been properly mounted to the device. More specifically, the syringe cover detection switch 24c is pressed and switched to the rear end side of the device by the other end of the syringe cover detecting lever 24a on the opposite side from the one end mentioned above, when the syringe cover 14 has been mounted.

The syringe holder spring 25 serves to bias the syringe holder 21 from the rear end side of the device toward the distal end side. One end thereof is linked to the rear end of the syringe holder 21, and the other end is fixed to a fixed wall inside the piston case 26.

The syringe holder 21 is a substantially cylindrical member used to support the preparation syringe 15, and is enclosed on the inner peripheral face side of the piston case 26. The syringe holder 21 has in its interior a piston 43, the syringe detection switch (syringe detector) 23, the syringe identifier 31, and a guide hole 42.

The piston 43 includes the piston 22 and the piston drive motor 27. The piston 22 is a disk-shaped member, moves forward while in contact with the rubber seal 15b provided to the rear end of the preparation syringe 15, and pushes out the preparation 29 toward the administration side. The piston drive motor 27 rotates in the desired direction, which causes the piston 22 to move back and forth in the direction of administration of the preparation 29.

The syringe detection switch 23 includes a protrusion that protrudes into the guide hole 42 and is pressed down by the syringe end face 15e of the preparation syringe 15 when the preparation syringe 15 is mounted to the syringe holder 21. Consequently, it can be detected from the operation of the switch that the preparation syringe 15 has been mounted in the syringe holder 21.

The syringe identifier 31 reads the ID 15d provided to the preparation syringe 15, detects that the preparation syringe 15 has been inserted, and determines the type of preparation syringe 15, etc. Also, part of the syringe identifier 31 is exposed at the guide hole 42, and contact between this exposed portion and the ID 15d provided to the preparation syringe 15 makes possible the identification of the ID 15d.

Figure 15:
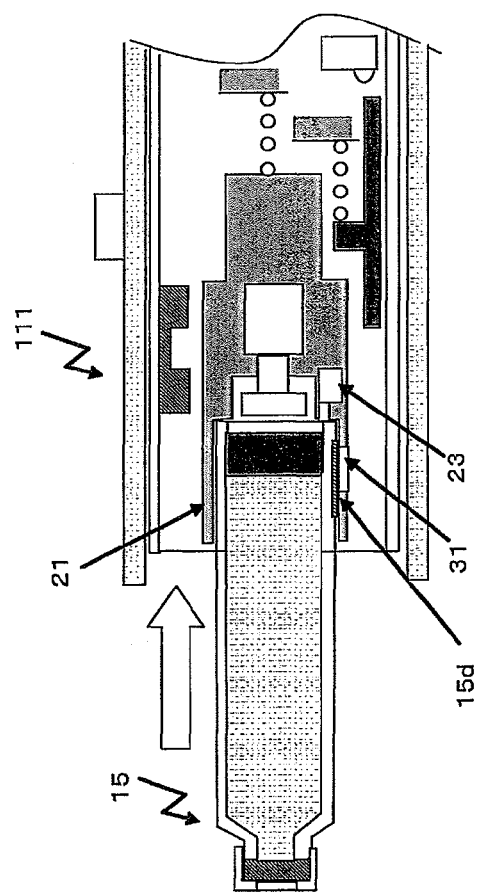
FIG. 15 is an internal cross section of a state in which the preparation syringe has been mounted in the syringe holder in the medication administering device in FIG. 14.
Figure 15:
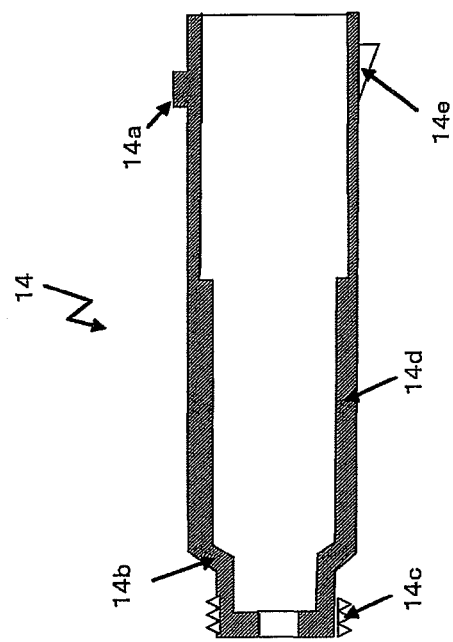

The guide hole 42 guides the preparation syringe 15 in the direction of the piston 43 while in contact with the outer peripheral face of the preparation syringe 15 when the preparation syringe 15 is mounted. This guide hole 42 is constituted by the inner peripheral face of the syringe holder 21 and the syringe receiving face 21a, which is substantially parallel to the face of the piston 22 that presses on the rubber seal 15b. Also, the guide hole 42 is formed so that when the preparation syringe 15 has been inserted into this guide hole 42, as shown in FIG. 15, the syringe end face 15e and the syringe receiving face 21a will come into contact, and the rubber seal 15b of the preparation syringe 15 and the piston 22 will be opposite each other with a tiny gap in between. This prevents the piston 22 from unintentionally pressing on the rubber seal 15b at the instant when the preparation syringe 15 is mounted.

Also, the outer peripheral face of the syringe holder 21 is formed so as to come into contact with the inner peripheral face of the syringe cover 14, and serves to guide the syringe cover 14 when the syringe cover 14 is mounted to the device. This guidance allows the syringe cover 14 to be mounted so that the detection tab 14e engages with the syringe cover detecting lever 24a, and the fastening tab 14a fits into the fastening groove 26a.

<Method for Operating the Medication Administering Device 111>

The method for operating the medication administering device 111 in this embodiment will now be described through reference to FIGS. 15 to 20.

First, as shown in FIG. 15, the preparation syringe 15 is inserted into the guide hole 42 of the syringe holder 21 (see FIG. 14). In the course of inserting the preparation syringe 15 here, the syringe end face 15e pushes down the syringe detection switch 23. Consequently, the medication administering device 111 detects from the operation of the switch that the preparation syringe 15 has been mounted.

The ID 15d provided to the preparation syringe 15 is then read by the syringe identifier 31, and the medication administering device 111 determines whether or not the inserted preparation syringe 15 contains the desired preparation.

No problem will be encountered here even if the insertion of the preparation syringe 15 should be inadequate and the syringe detection switch 23 cannot be switched or the syringe identifier 31 cannot read. The following description will include this scenario.

Figure 16:
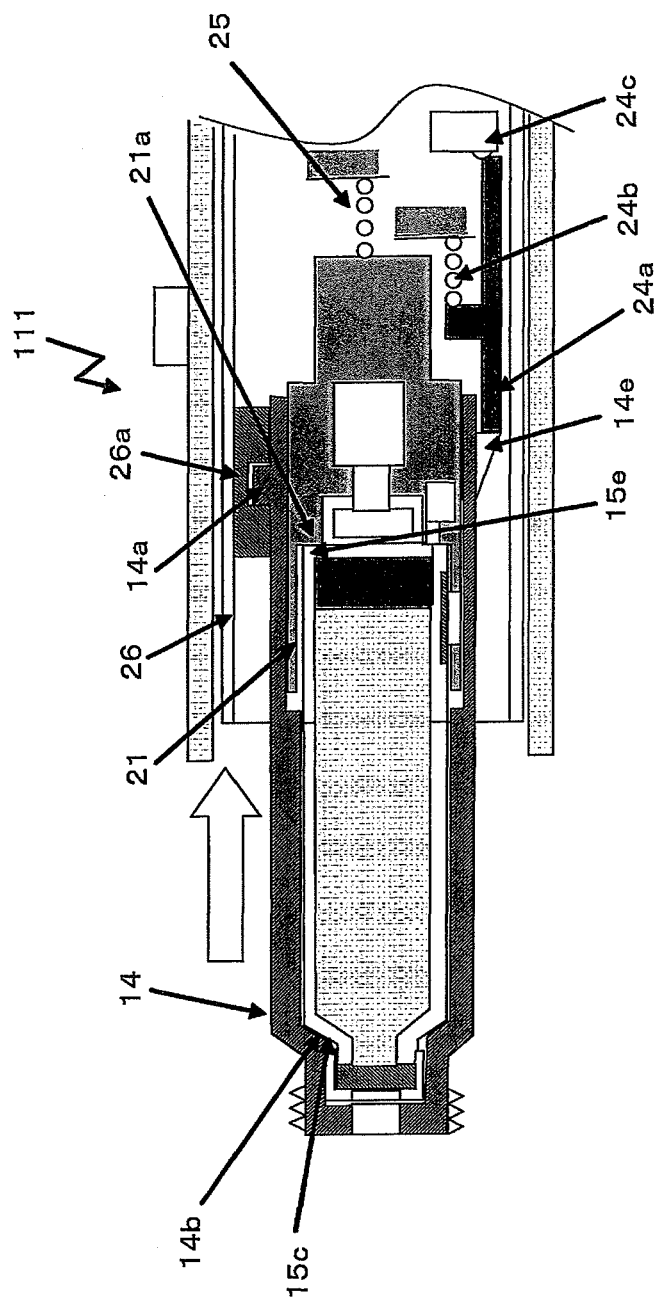
FIG. 16 is an internal cross section of a state in which the syringe cover has been mounted to the main body in the medication administering device in FIG. 14.

Next, as shown in FIG. 16, the syringe cover 14 is mounted inside the piston case 26. At this point the fastening tab 14a and the fastening groove 26a fit together, and the syringe cover 14 is fixed inside the piston case 26.

Here, the syringe contact-use inclined part 14*b* provided to the syringe cover 14 pushes the syringe cover contact-use inclined part 15*c* provided to the preparation syringe 15 in the direction of the rear end when the fastening tab 14*a* and the fastening groove 26*a* are fitted together and the syringe cover 14 is fixed. Therefore, the syringe end face 15*e* pushes the syringe receiving face 21*a*, and the syringe holder 21 is slid in the rear end direction (the direction of the right-facing arrow in FIG. 16). Also, at this point the syringe holder spring 25 is held in a compressed state. Therefore, even if the preparation syringe 15 should not be inserted sufficiently in the previous operation, the mounting of the syringe cover 14 will effectively bring about the above-mentioned switching of the syringe detection switch 23 and reading by the syringe identifier 31.

Also, when the syringe cover 14 is mounted, the detection tab 14*e* pushes the syringe cover detecting lever 24*a* in and switches the syringe cover detection switch 24*c*. This allows the drug administration device 111 to detect that the syringe cover 14 has been mounted. The syringe cover detecting lever spring 24*b* at this point is held in a compressed state.

Figure 17:
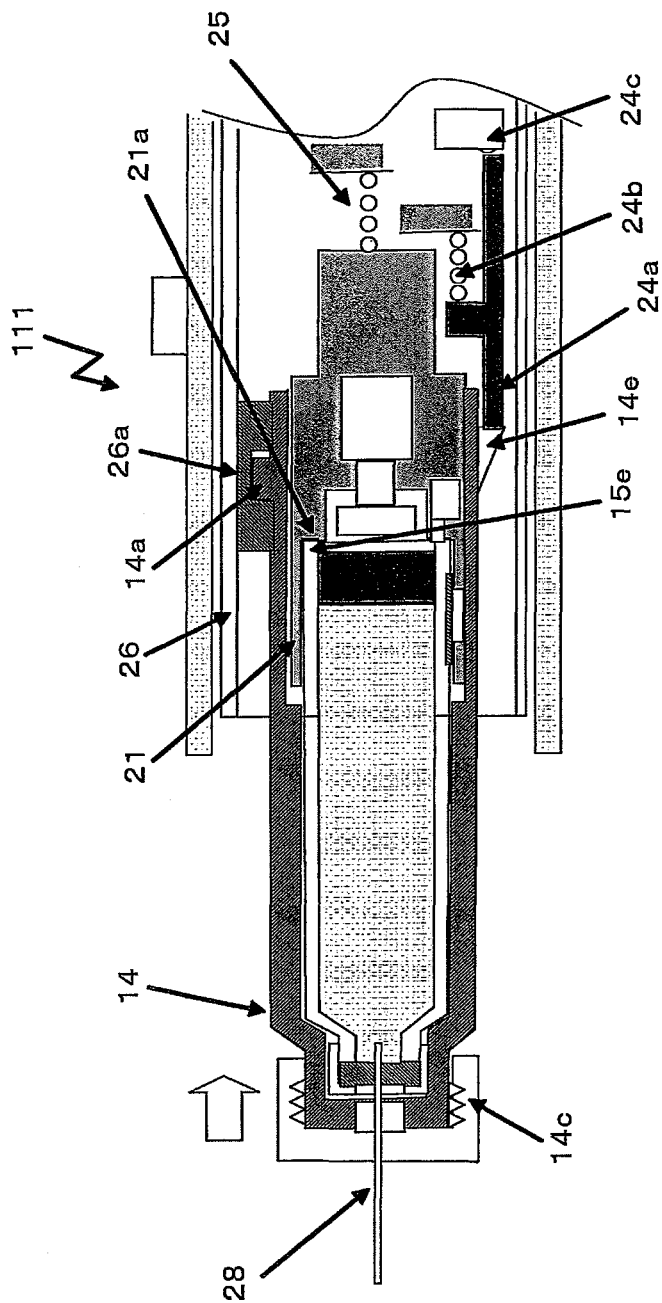
FIG. 17 is an internal cross section of a state in which the puncture needle has been mounted in the medication administering device in FIG. 14.

Then, as shown in FIG. 17, a puncture needle 28 that is stuck into the body of a person, etc., and injects a medication solution from the puncture tip is placed in the puncture needle mounting portion 14*c* at the distal end of the preparation syringe 15.

Figure 18:
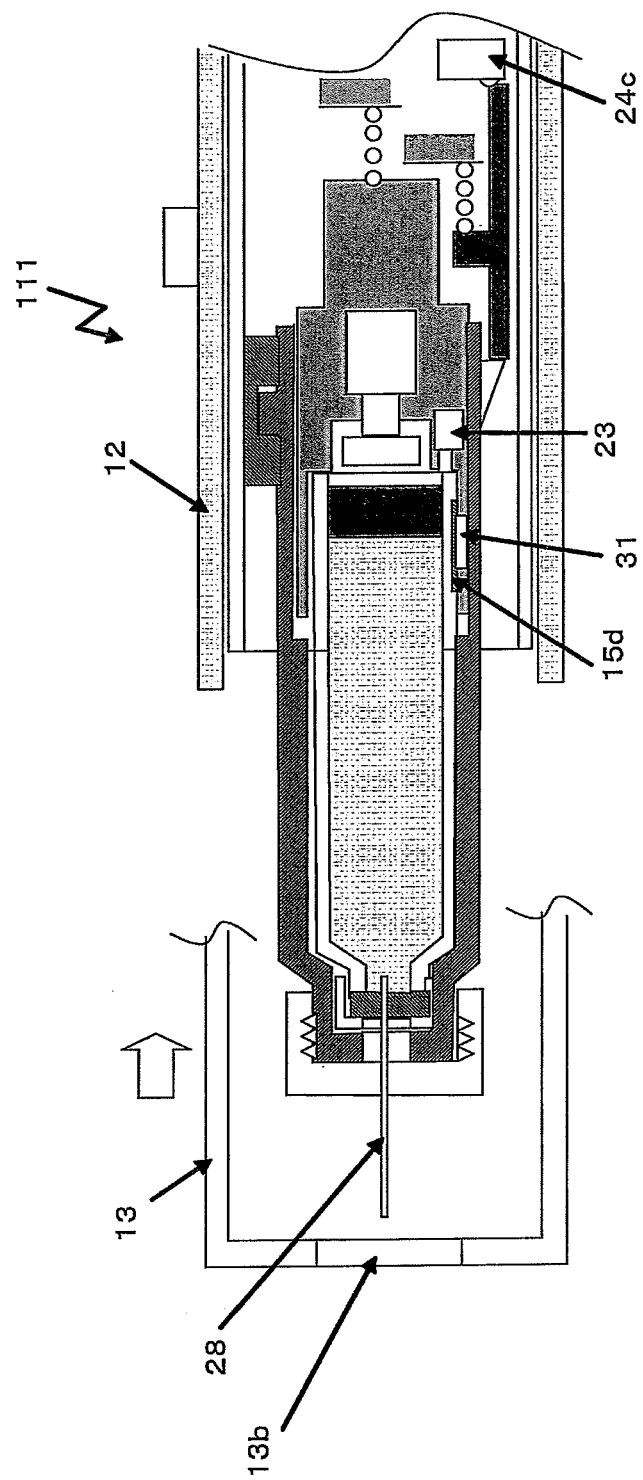
FIG. 18 is an internal cross section of a state in which the distal end cap has been mounted in the medication administering device in FIG. 14.

Then, as shown in FIG. 18, the distal end cap 13 that is in contact with the skin of a person, etc., is mounted to the distal end of the housing 12 on the medication administration side. An opening 13*b* through which the puncture needle 28 passes is formed in the center of the distal end cap 13.

After the pre-use preparation has been performed as discussed above by going through the steps described through reference to FIGS. 15 to 18, the power button 16 (see FIG. 2) is pressed to supply power to the medication administering device 111. At this point the medication administering device 11 checks the status of the syringe detection switch 23 and the syringe cover detection switch 24*c*, and checks whether or not the preparation syringe 15 or the syringe cover 14 has been mounted. The syringe identifier 31 reads information about the ID 15*d* of the preparation syringe 15, and it is confirmed whether or not the correct preparation syringe 15 has been mounted in the medication administering device 111. On the condition that all of these checks have been completed, the drug administration device 111 is ready for the air vent button 17 to be pressed in the next operation (see FIG. 2).

Next, when the air vent button 17 is pressed, a piston case drive motor (not shown) slides the entire piston case 26 by approximately 10 mm to the left (the distal end direction) with respect to the housing 12. The piston drive motor 27 is then actuated, and the piston 22 moves by a specific amount to the left (the distal end direction) to vent air. At this point, the rubber seal 15*b* is pushed in the puncture direction (to the left in the drawings), and the air inside the preparation syringe 15 is discharged from the puncture needle 28. After this, the piston case drive motor is reversed, and the entire piston case 26 slides 10 mm to the right, which is the opposite direction from the puncture direction (the rear end direction), with respect to the housing 12, thus returning to its original position.

Figure 19:
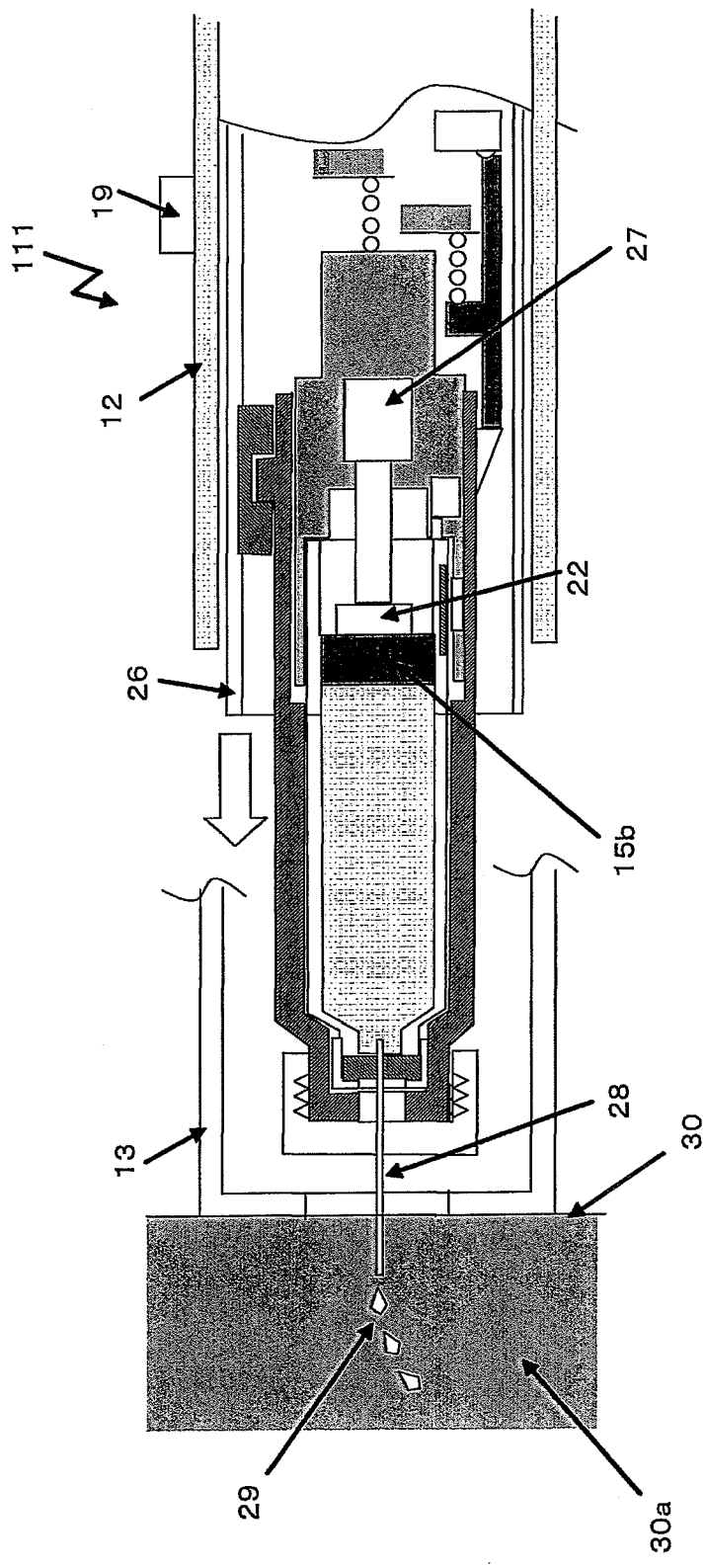
FIG. 19 is an internal cross section of the administration state of the medication administering device in FIG. 14.

Next, as shown in FIG. 19, the flow moves to a step of administering the preparation, but the basic operation is the same as that of the air venting discussed above.

That is, when the distal end cap 13 is brought into contact with the skin 30 and the medication administering button 19 is pressed, the piston case drive motor (not shown) slides the entire piston case 26 by approximately 10 mm in the puncture direction (to the left in the drawings) with respect to the housing 12. The distal end of the puncture needle 28 is exposed from the distal end cap 13 and reaches the subcutaneous layer 30*a* from the skin 30.

Next, the piston drive motor 27 is actuated, the piston 22 moves a specific amount for preparation injection in the puncture direction (to the left in the drawings), and the rubber seal 15*b* is pushed in in the puncture direction (to the left in the drawings). As a result, the preparation 29 inside the preparation syringe 15 is injected from the puncture needle 28 to the subcutaneous layer 30*a*.

Figure 20:
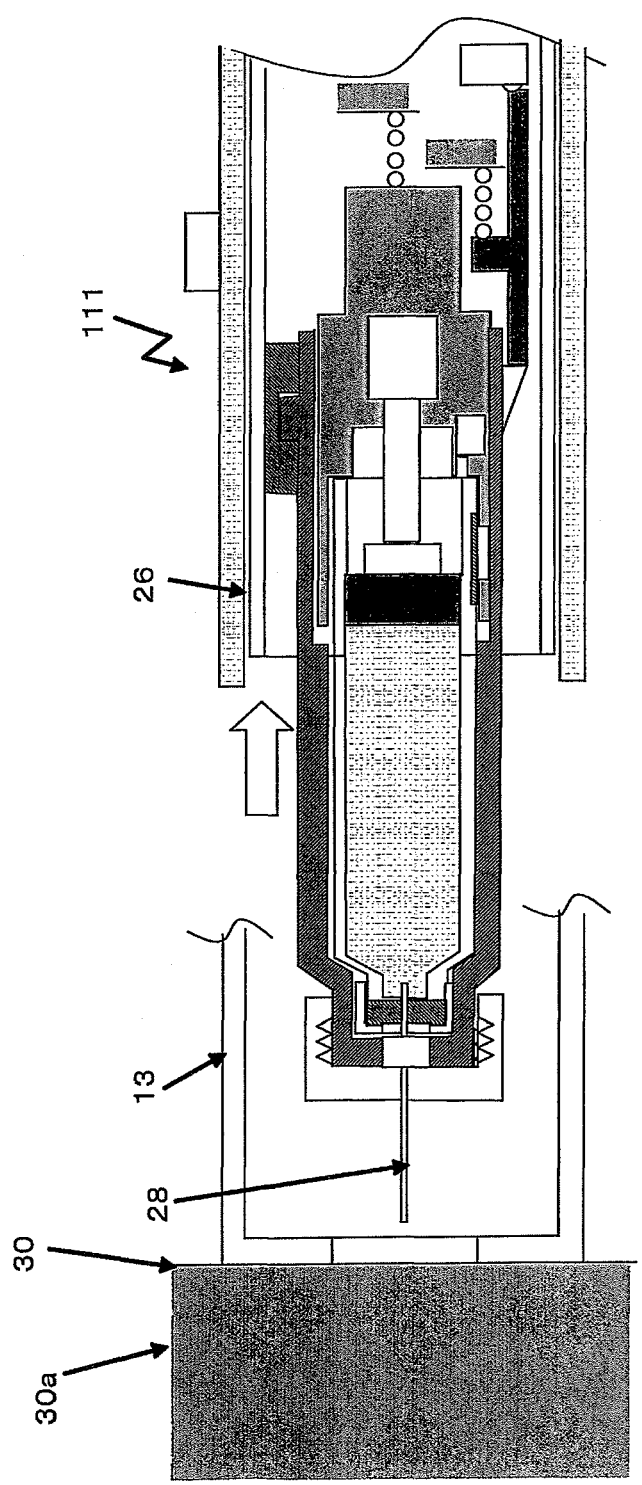
FIG. 20 is an internal cross section of the state after administration with the medication administering device in FIG. 14.

After this, as shown in FIG. 20, the piston case drive motor is reversed, and the entire piston case 26 slides approximately 10 mm in the opposite direction from the puncture direction (to the right in the drawings) with respect to the housing 12, thus returning to its original position. Therefore, the puncture needle 28 is pulled out of the skin 30 or subcutaneous layer 30*a*, and put back inside the distal end cap 13.

As discussed above, with this embodiment, the medication administering device 111, to which the preparation syringe 15 containing the preparation 29 is mounted, and which is able to administer the preparation 29 to a living body or the like, comprises the syringe holder spring 25 that biases the syringe holder 21 from one direction, the syringe cover 14 that covers the preparation syringe 15 and to the distal end of which the puncture needle 28 can be removably attached, and the syringe holder 21 to which the preparation syringe 15 and the syringe cover 14 are removably mounted.

Consequently, attachment and removal of the preparation syringe 15 can be accomplished easily and reliably.

Also, with this embodiment, the syringe detection switch 23 is provided inside the syringe holder 21, which allows the mounting of the preparation syringe 15 to be detected reliably.

Also, with this embodiment, the syringe identifier 31 is provided inside the syringe holder 21, which means that the ID of the preparation syringe 15 can be read, and whether or not the correct preparation syringe 15 has been mounted can be detected. Further, with this embodiment, the syringe cover detector 24 is provided inside the piston case 26, which allows the mounting of the syringe cover 14 to be detected reliably.

Thus, because of these detection functions, a safe medication administering device can be provided which will not be accidentally operated at any unintended places.

(Embodiment 4)

The configuration of a syringe holder 212 used in a medication administering device pertaining to another embodiment of the present invention will be described below through reference to FIG. 21. Those components that are shared with the above-mentioned Embodiments 1 to 3 will be numbered the same and not described again.

Figure 21:
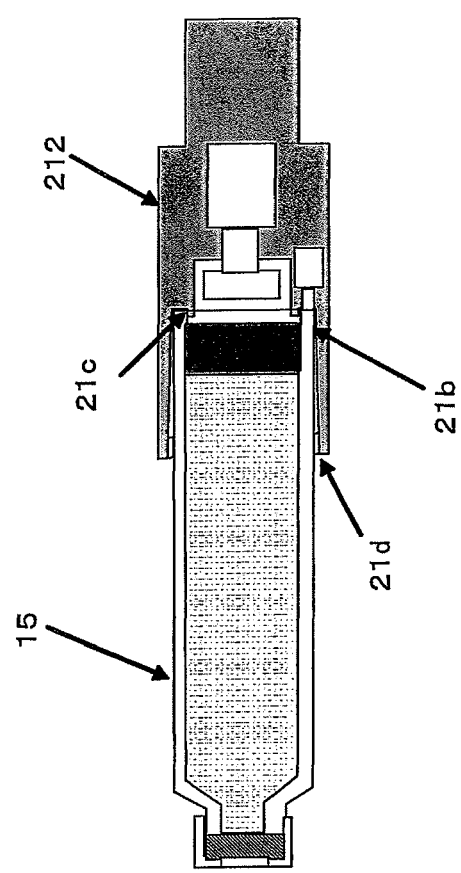
FIG. 21 is an internal cross section of the syringe holder and the preparation syringe of the medication administering device pertaining to Embodiment 4 of the present invention.

With the syringe holder 212 in this embodiment, as shown in FIG. 21, the difference from Embodiment 3 above is that an outer peripheral limiting protrusion 21*d* that supports the outer peripheral face of the preparation syringe 15, and an inner peripheral limiting protrusion 21*c* that limits the position of the inner peripheral face of the preparation syringe 15 are provided.

Consequently, positioning is easier and more accurate when the preparation syringe 15 is inserted into the guide hole, and the preparation syringe 15 can be supported more securely. Also, when the preparation syringe 15 is inserted into the syringe holder 21, a gap is formed at the portion where the outer peripheral limiting protrusion 21*d* is not formed, so that the inner peripheral face of the syringe holder 21 and the outer peripheral face of the preparation syringe 15 do not come into contact. Therefore, in inserting the preparation syringe 15 into the syringe holder 21, the inside of the syringe holder 21 is not in a sealed state, so inserting and removing the preparation syringe 15 can be made easier.

Furthermore, the syringe holder 212 has a guiding inclined portion (tapered portion) 21b that has a tapered shape so that the preparation syringe is easier to guide in the piston direction during insertion of the preparation syringe 15. Consequently, the positional accuracy when inserting the preparation syringe 15 is even better than in Embodiment 3 above.

Also, the medication administering device in this embodiment is the medication administering device pertaining to the embodiments given above, wherein all or part of the syringe cover is transparent or semitransparent.

Consequently, the interior of the syringe cover can be checked, so in a state in which the preparation syringe is mounted to the syringe holder, and the preparation syringe is covered by the syringe cover, the type of preparation syringe, whether or not there is a preparation syringe, the amount of remaining preparation, and so forth can be checked visually.

The medication administering device in this embodiment is the medication administering device pertaining to the embodiments given above, further comprising a syringe cover detector that detects that the syringe cover has been mounted.

Consequently, whether or not the syringe cover has been mounted to the device main body can be detected, and therefore, operation of the medication administering device can be prevented in a state in which the syringe cover is not yet mounted, for example.

As a result, the user is prevented from accidentally operating the device without the syringe cover (and the preparation syringe) having been mounted, so the safety of the device can be improved.

The medication administering device in this embodiment is the medication administering device pertaining to the embodiments given above, wherein syringe cover detector includes a syringe cover detecting lever, a syringe cover detecting lever spring, and a syringe cover detecting switch. The syringe cover detecting lever spring biases the syringe cover detecting lever from one direction. The syringe cover detecting switch is switched on and off by the syringe cover detecting lever.

Consequently, whether or not the syringe cover has been mounted can be detected with a simple configuration. Therefore, the user can be prevented from accidentally operating the device without the syringe cover having been mounted.

REFERENCE EXAMPLE 1

A medication administering device with which the needle was pulled out after the needle is tapped to a living body by electrically-driven means and injection of the preparation has been put to practical use in the past as a medication administering device for easily administering a preparation to a living body.

Figure 22:
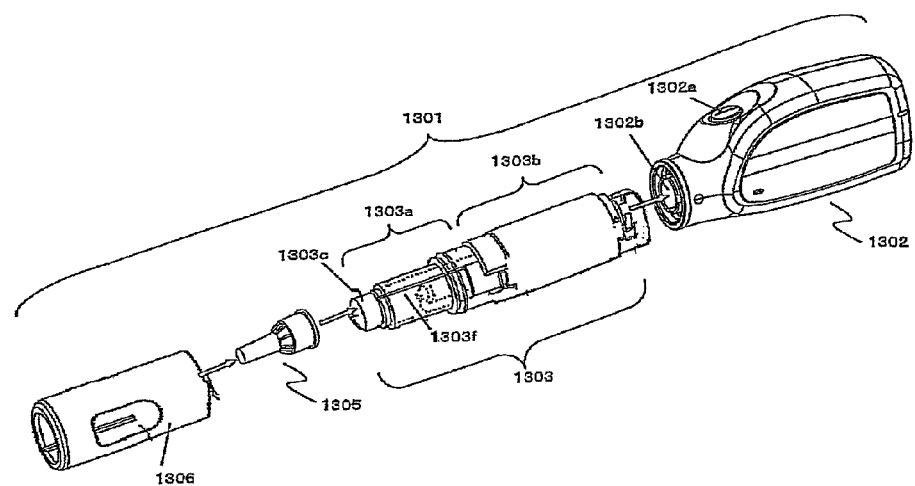
FIG. 22(a) is an exploded oblique view of a medication administering device given as a reference example.
FIG. 22(b) is a diagram of the constituent parts of the needle portion used in the medication administering device.
FIG. 22(c) is an exploded oblique view of the front portion of a medication administering device given as a reference example.
Figure 22:
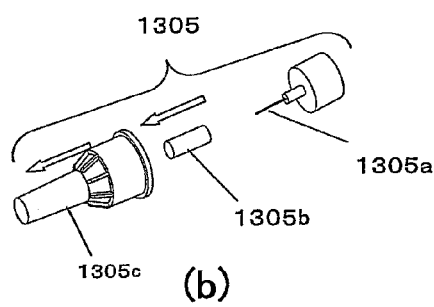
Figure 22:
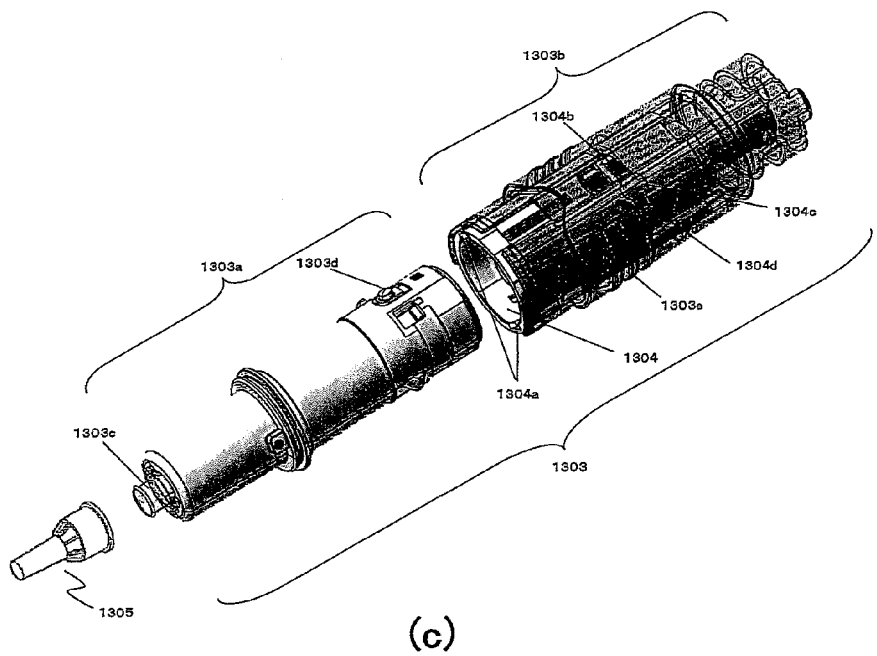

Specifically, as shown in FIGS. 22(a) to 22(c), when a medication administering device 1301 such as this is used, the user first mounts a syringe 1303a to a front case component 1303b, and then mounts this front component 1303 to a main body 1302 that includes a medication administering button 1302a for pushing out a piston 1302b. A preparation syringe 1303f has rubber seals (not shown) on the distal end side and the rear end side. The rubber seals are pressed and deformed in the distal end direction by the piston 1302b, and along with this deformation the preparation is injected into the living body. Also, the front case component 1303b is constituted by a front case 1303e that covers the outside, and a slide case 1304 or the like that slides on the inside thereof.

The syringe 1303a has a needle mounting portion 1303c to which a needle 1305 can be removably attached, and a dowel 1303d that fits into a guide groove 1304a of the slide case 1304 (see Japanese Laid-Open Patent Application 2005-287676, for example).

However, with the conventional medication administering device 1301, as shown in FIG. 22(c), the user first inserts the dowel 1303d provided to the syringe 1303a straight into the guide groove 1304a of the slide case 1304 that is part of the front case component 1303b, and then rotates this so that a dowel pressing portion 1304c passes through a hole A (indicated by 1304b) provided to the slide case 1304, and is fixed in a hole B (1304d). Next, the needle 1305 for injecting the preparation is attached to the needle mounting portion 1303c. After this, the front component 1303 is mounted to the main body 1302, a front cap 1306 is mounted to the front case component 1303b, the distal end of the front cap 1306 is brought into contact with the subject's body, and in this state the medication administering button 1302a is pressed to inject the preparation.

With the conventional usage method discussed above, it is dangerous if the syringe 1303a moves away from the slide case 1304 in the removal of the needle 1305a from the needle mounting portion 1303c, so it has to be fixed securely. The attachment and removal of the syringe 1303a required a great deal of strength, so the device was difficult to use. Also, since the dowel 1303d was forcibly deformed and fixed by the dowel pressing portion 1304c, there was the risk of damage during use.

The medication administering device pertaining to the following embodiment solves the above-mentioned problem, and it is an object thereof to provide a medication administering device for injecting a preparation into a living body, wherein the syringe is easy to attach and remove, is securely fixed, and is durable.

(Embodiment 5)

A medication administering device 320 pertaining to yet another embodiment of the present invention will now be described through reference to FIGS. 23 to 26(a).

Figure 23:
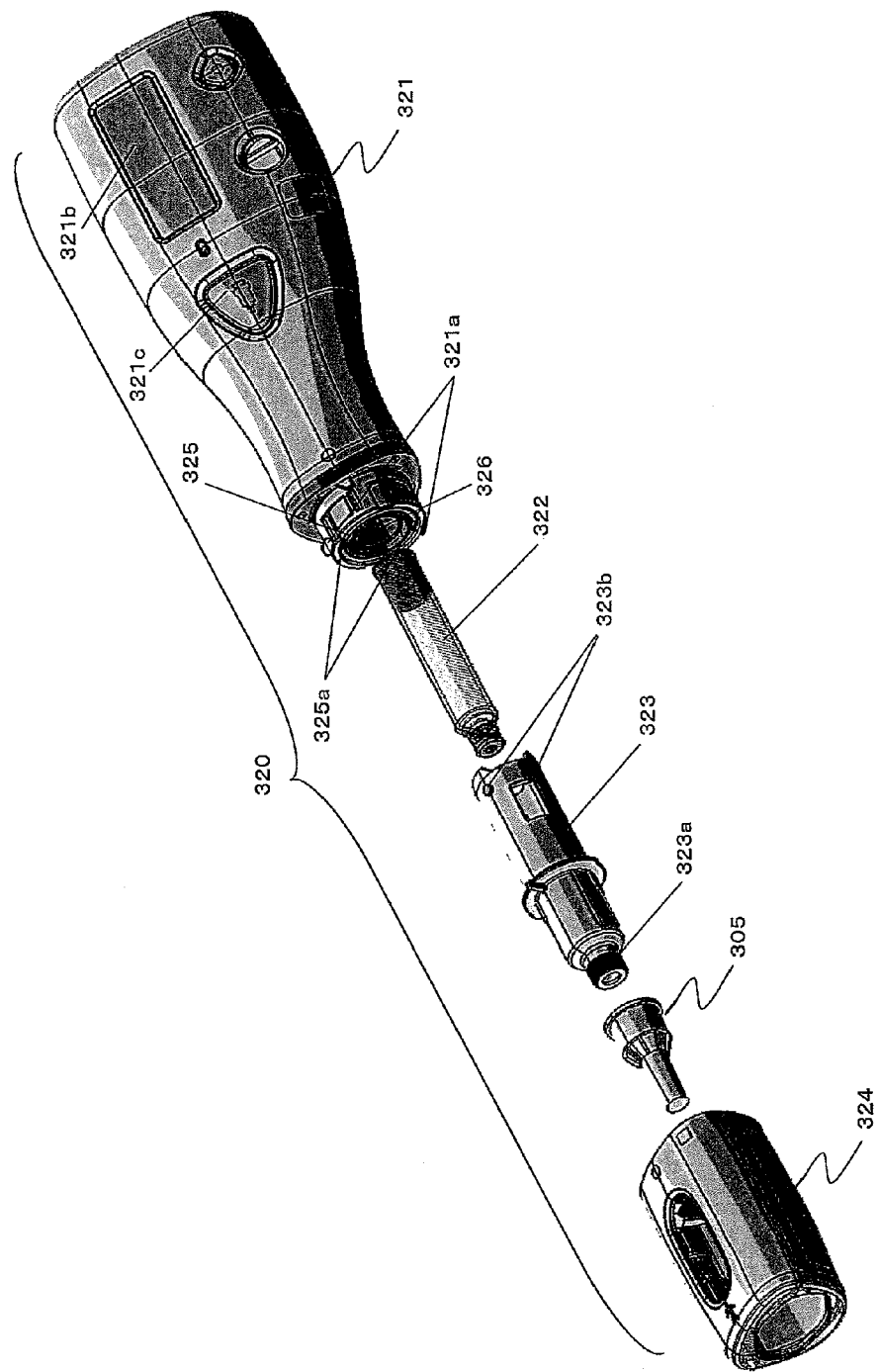
FIG. 23 is an exploded oblique view of the medication administering device in Embodiment 5 of the present invention.
Figure 24:
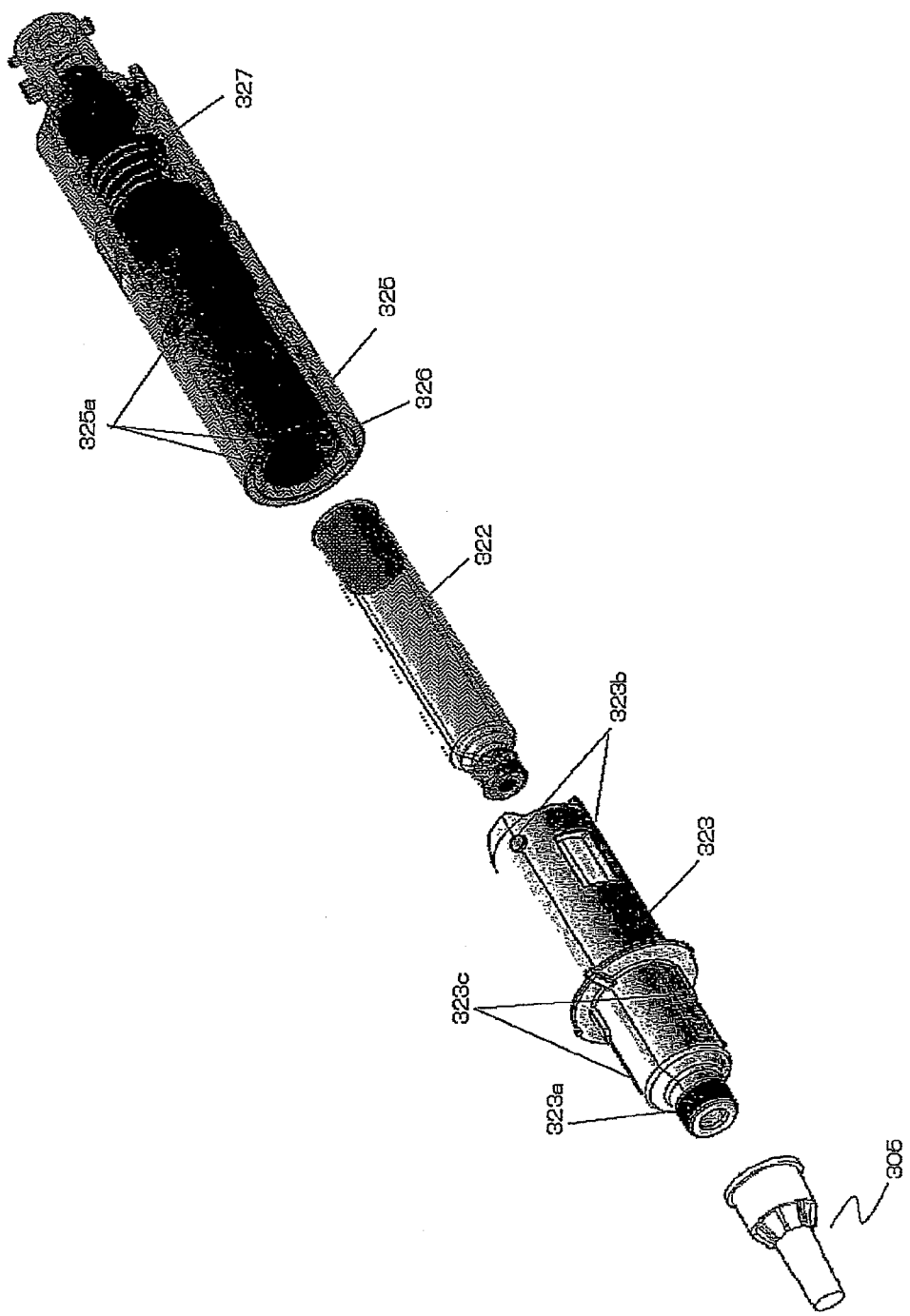
FIG. 24 is an exploded oblique view of the area around the inner case of the medication administering device shown in FIG. 23.
Figure 25:
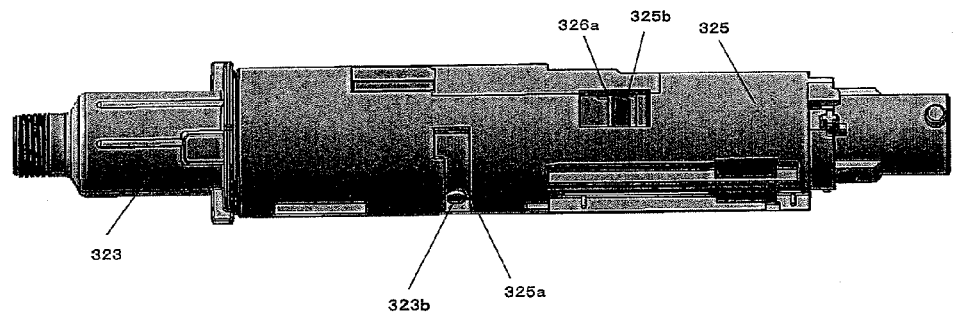
FIG. 25(a) is a diagram in which the syringe cover has been mounted to the inner case with the medication administering device shown in FIG. 23.
FIG. 25(b) is a diagram in which the syringe cover has been inserted with the medication administering device shown in FIG. 23.
FIG. 25(c) is a diagram in which the syringe cover has been mounted with the medication administering device shown in FIG. 23.
Figure 25:
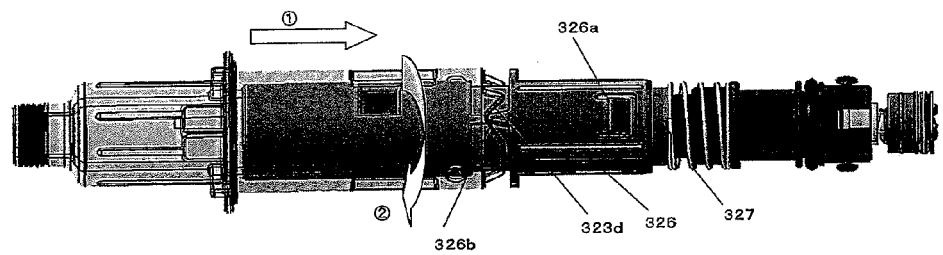
Figure 25:
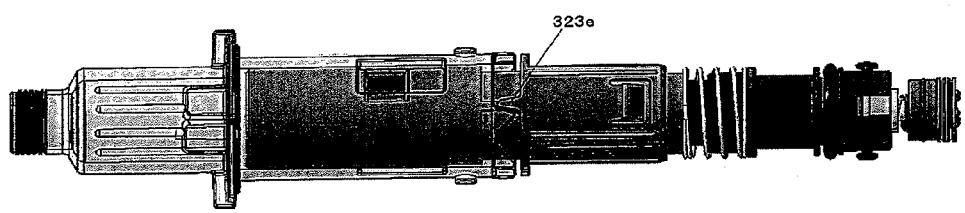
Figure 26:
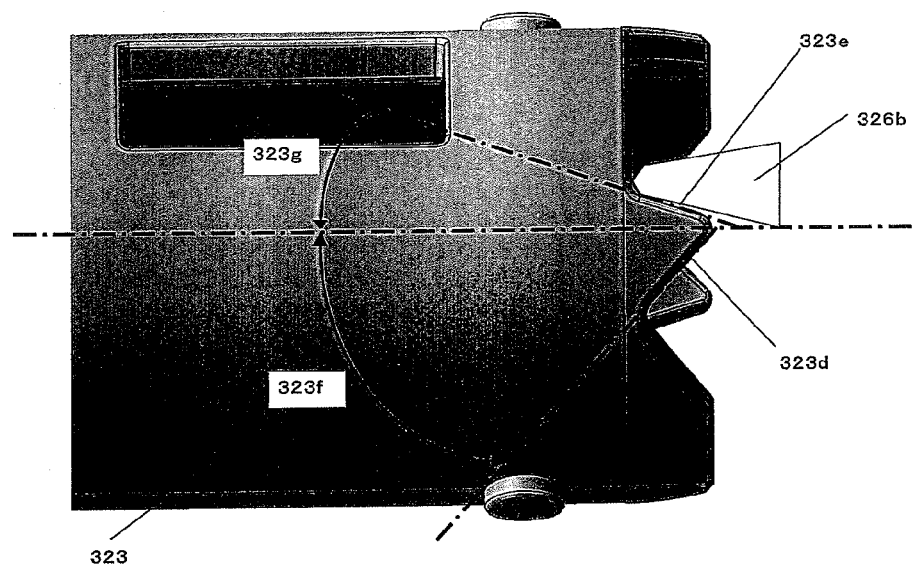
FIG. 26(a) is a diagram of the relation between the end of the syringe holder and the syringe cover in Embodiment 5.
FIG. 26(b) is a diagram of the relation between the end of the syringe holder and the syringe cover in Embodiment 6.
Figure 26:
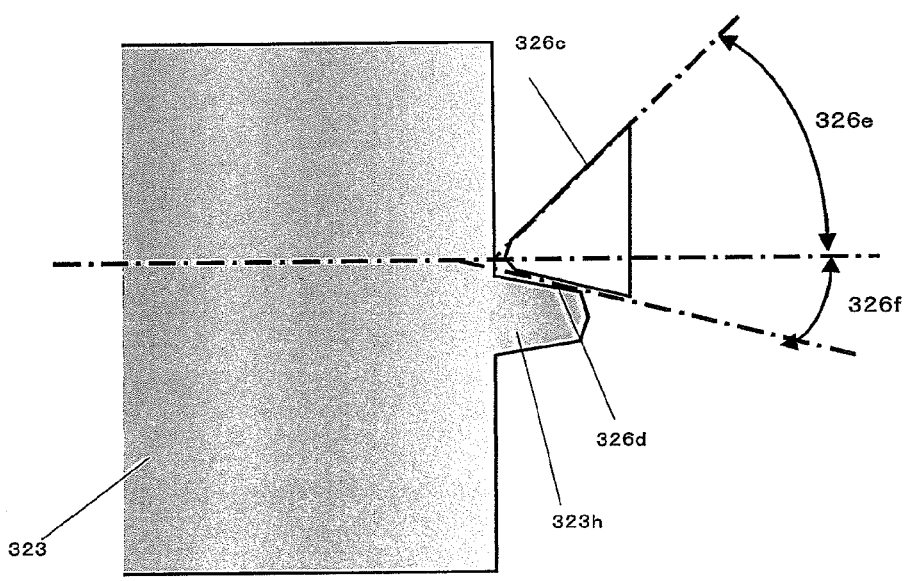

As shown in FIG. 23, the medication administering device 320 in this embodiment is mainly constituted by a main body 321, a preparation syringe 322, a syringe cover 323, a needle 305, and a distal end cap 324.

The main body 321 is constituted by a positioning mark 321a that serves as a benchmark in inserting a fastening dowel 323b of the syringe cover 323, a medication administering button 321c used in administering the preparation, a display component 321b that displays the remaining battery charge and various information required for operation, a syringe holder 326 that temporarily supports the preparation syringe 322, an inner case 325 that is able to slide with respect to the main body 321, and a syringe cover fastening groove 325a that is a guide groove for guiding the fastening dowel 323b provided to the syringe cover 323.

The inner case pertaining to this embodiment, and its surroundings, will now be described through reference to FIGS. 24 to 26(a).

The syringe cover 323 is a transparent or semitransparent member that can be mounted to the inner case 325 from the distal end side of the preparation syringe 322 temporarily supported by the syringe holder 326, and has formed at one end a needle mounting portion 323a for mounting the needle 305. At the other end is a mounting direction inclined face 323d used in the mounting of the syringe holder, and a removal direction inclined face 323e used in the removal of the syringe holder, and the inclination angles of these two are different, as indicated by the mounting direction inclination angle 323f and the removal direction inclination angle 323g. The fastening dowel 323b is guided by the syringe cover fastening groove 325a provided to the inner case 325. An anti-slip rib 323c is provided to the outer peripheral part that supports during attachment and removal.

The distal end cap 324 is mounted after the preparation syringe 322, the syringe cover 323, and the needle 305 have been mounted to the main body 321 in that order.

The inner case 325 is able to slide with respect to the main body 321, and constitutes the syringe holder 326 that supports the preparation syringe 322 in its interior, and a syringe holder biasing spring 327 that biases this from one direction.

The syringe holder 326 is in a cylindrical shape capable of supporting the preparation syringe 322 in its interior, and as shown in FIG. 25(a), a syringe holder prong 326a provided to part of the syringe holder 326 fits into a prong guide hole 325b provided to the inner case 325. At this point the syringe holder 326 slides under the force of the syringe holder biasing spring 327, and then maintains the fitted state. The syringe holder 326 also has a peaked convex portion 326b that has a substantially triangular shape and comes into contact with the mounting direction inclined face 323d and the removal direction inclined face 323e.

The syringe holder biasing spring 327 is slightly compressed when placed between the inner case 325 and the syringe holder 326, and biases the syringe holder 326 so as to slide.

<Method for Operating the Medication Administering Device 320>

The operation of the medication administering device 320 in an embodiment of the present invention will now be described through reference to FIGS. 23 to 26(a).

First, the preparation syringe 322 is inserted into the syringe holder 326 provided to the main body 321, and the syringe cover 323 is mounted. At this point the fastening dowel 323b is aligned with the syringe cover fastening groove 325a provided to the inner case 325, inserted straight in, and then rotated.

When the syringe holder 326 is rotated in the mounting direction by the syringe cover 323, the mounting direction inclined face 323d pushes the peaked convex portion 326b and compresses the syringe holder biasing spring 327. The effect of this is that a load is exerted on the rotation of the syringe holder 326, and as shown in FIG. 26(a), the mounting direction inclination angle 323f is set to a gentle angle, so the syringe holder 326 can be slid and mounted by rotating with just a light effort.

At the position where the syringe cover 323 is mounted, it is biased in the removal direction by the syringe holder 326 and the syringe holder biasing spring 327, but as shown in FIG. 25(a), the fastening dowel 323b is guided and supported by the syringe cover fastening groove 325a.

When the syringe holder 326 is rotated in the removal direction, the removal direction inclined face 323e pushes the peaked convex portion 326b and compresses the syringe holder biasing spring 327. The effect of this is that a load is exerted on the rotation of the syringe holder 326, and the removal direction inclination angle 323g is set to a sharp angle, so the syringe holder 326 cannot be slid off unless it is rotated with a strong effort (see FIG. 26(a)).

To create a relation in which the effort to remove the syringe cover 323 is greater than the effort to remove the needle 305, in this embodiment the values of the syringe holder biasing spring 327 and the removal direction inclination angle of the syringe cover 323 are adjusted with respect to a limit (namely, effort to remove the needle 305 is 0.1 N·m or less), and it is ensured that the effort to remove the syringe cover 323 will be at least 0.13 N·m. Meanwhile, the effort to mount the syringe cover 323 is about 0.05 N·m, so the syringe cover 323 can be mounted with light effort, but can only be removed with a strong effort.

In other words, the following relation is satisfied.

effort to attach syringe cover effort to remove needle <effort to remove syringe cover Next, the needle 305 is rotated and attached to the needle mounting portion 323a at one end of the syringe cover 323, the distal end cap 324 is mounted, and the protective cap and needle cap are taken off, which completes the pre-preparation for administering the medication solution.

As discussed above, in this embodiment, the medication administering device 320, to which is mounted the preparation syringe 322 containing a preparation and which administers the preparation to a living body, comprises the main body 321, the inner case 325 that forms the main body 321, the syringe holder 326 that is installed inside the inner case 325 and supports the preparation syringe 322, the syringe holder biasing spring 327 that biases the syringe holder 326, and the syringe cover 323 that covers the preparation syringe 322. The syringe cover 323 has uneven faces of different angles of inclination on its end face, and mounts the preparation syringe to the main body in conjunction with the inner case 325 in a state in which the needle that administers the preparation can be attached and removed.

Consequently, there is provided a durable medication administering device 320 in which the syringe cover 323 is easy to attach and remove and is securely fixed during mounting.

(Embodiment 6)

The configuration of the syringe cover 323 and the syringe holder 326 constituting a medication administering device pertaining to yet another embodiment of the present invention will be described through reference to FIG. 26(b).

In this embodiment, a peaked convex portion 323h is formed at one end of the syringe cover 323. Also, the syringe holder 326 is given a shape that has a mounting direction inclined face 326c and a removal direction inclined face 326d which come into contact with the peaked convex portion 323h, and when the syringe cover 323 rotates, it can be pushed and slid by the peaked convex portion 323h. A mounting direction inclination angle 326e is set to a gentle angle with respect to the peaked convex portion 323h, so the syringe holder 326 can be slid by lightly rotating the syringe cover 323. On the other hand, a removal direction inclination angle 326f is set to a sharp angle with respect to the peaked convex portion 323h, and the syringe holder 326 cannot be slid unless the syringe cover 323 is rotated with effort.

Consequently, just as in Embodiment 5 above, there is provided a durable medication administering device in which the syringe cover 323 is easy to attach and remove and is securely fixed during mounting.

Also, the medication administering device of this embodiment is the medication administering device pertaining to the embodiments given above, wherein the syringe cover is a transparent member or a semitransparent member with which the preparation inside the preparation syringe can be visually checked.

This means that the type of preparation that has been mounted, and the remaining amount of preparation can be checked without having to remove the syringe cover, which makes the device more convenient to use.

The medication administering device of this embodiment is the medication administering device pertaining to the embodiments given above, wherein a first force required in mounting the syringe cover to the inner case is set to be different from a second force required in removing the syringe cover from the inner case.

Consequently, the force required for removal is greater than the force required for mounting, which means that the syringe cover is easy to attach but will not readily come off, which facilitates operation and improves reliability.

With the medication administering device of the present invention, there is provided a medication administering device that injects a preparation into a living body, wherein this medication administering device is durable and the syringe can be easily attached and removed and can be securely fixed.

REFERENCE EXAMPLE 2

A medication administering device with which the puncture needle was electrically inserted into the living body and then removed after injection of the preparation has been put to practical use in the past as a medication administering device for easily administering a preparation to a living body.

Figure 27:
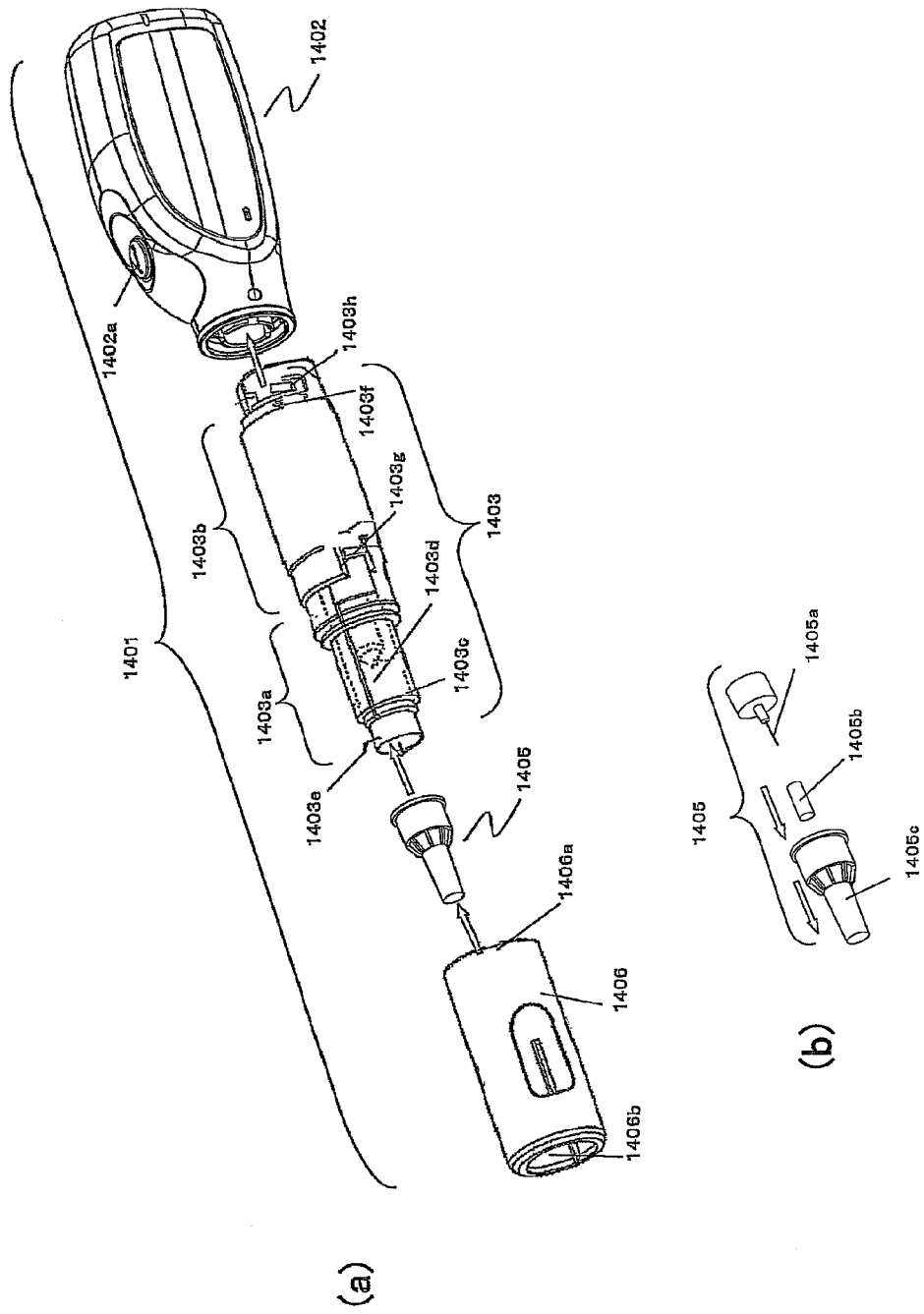
FIG. 27(a) is an exploded oblique view of a medication administering device given as a reference example.
FIG. 27(b) is a diagram of the constituent parts of the needle portion used in the medication administering device.

Specifically, as shown in FIG. 27($a$), when this medication administering device 1401 is used, the user first docks a syringe 1403$a$ and a front case component 1403$b$. In between these two, a slidably constituted front component 1403 is mounted to a main body 1402. At this point, a fastening groove 1403$f$ formed at one end of the front case component 1403$b$ allows the attachment and removal of the front case component 1403$b$ and the main body 1402. The members constituted by the syringe 1403$a$ and the members constituted by the main body 1402 are then linked, and the syringe 1403$a$ is able to slide (not shown). A switch (not shown) that detects the attachment and removal of the front component 1403 is provided to the main body 1402, and is switched on and off by operation of a front component detecting lever 1403$h$.

After this, a needle portion 1405 is rotated and attached to a needle mounting portion 1403$e$, and a front cap 1406 is inserted straight into the front case component 1403$b$. The outer shape of the front cap 1406 is substantially cylindrical, and a detecting lever pusher 1406$a$ at one end thereof slides a front cap detecting lever 1403$g$ and switches a detection switch (not shown) provided to the main body 1402.

Here, as shown in FIG. 27($b$), the needle portion 1405 is constituted by a needle 1405$a$, a needle cap 1405$b$, and a protective cap 1405$c$. The needle mounting portion 1403$e$ is provided at one end of a preparation syringe 1403$d$ mounted in a housing 1403$c$ that constitutes the syringe 1403$a$ (see Japanese Laid-Open Patent Application 2005-287676, for example).

However, with the conventional medication administering device 1401, the user first aligns the fastening groove 1403$f$ of the front component 1403, which holds the preparation syringe 1403$d$, with a tab (not shown) provided to the main body 1402. Then, the needle portion 1405 for injecting the preparation is attached to the needle mounting portion 1403$e$, and the front cap 1406 is mounted to the front case 1403$b$. The front cap 1406 is used both for safety and as the part that comes into contact with the skin, so it needs to be mounted. After this, the protective cap 1405$c$ and the needle cap 1405$b$ are removed through a front cap opening 1406$b$.

After these operations have been performed, when a medication administering button 1402$a$ on the main body 1402 is pressed, the syringe 1403$a$ slides, the injection needle 1405$a$ is exposed by a few millimeters from the distal end of the front cap 1406, and the injection needle 1405$a$ is stuck into the skin. In this state, the required amount of medication is injected from the preparation syringe 1403$d$, after which the syringe 1403$a$ slides back to its original position, the needle 1405$a$ returns from the front cap 1406, the injection needle is removed from the skin, and the administration operation is concluded.

The situation in which this series of operations is performed is when the front component 1403 has been properly mounted to the main body 1402, the detecting switch (not shown) on the main body 1402 has been switched on by the detecting lever 1403$h$, the front cap 1406 has been properly mounted to the front component 1403, and the front cap detecting lever 1403$g$ has switched on the detecting switch (not shown) provided to the main body 1402.

With the conventional usage method discussed above, as shown in FIG. 27($a$), even if the front component 1403 has not been completely mounted, an error is detected only after the front cap 1406 has been mounted, and the medication administering button 1402$a$ on the main body 1402 of the medication administering device 1401 has been operated. To remount the front component 1403, the front cap 1406 first has to be removed, or the front component 1403 removed, so the problem is that this takes more time.

The following embodiment solves the above problem, and it is an object thereof to provide a medication administering device for injecting a preparation into a living body, wherein even if the mounting of the front component is incomplete, if the front cap is properly mounted, the front component will be forcibly mounted, so improper mounting is far less likely to occur, reliability is improved, and the medication administering device is easier to operate.

(Embodiment 7)

A medication administering device 420 pertaining to yet another embodiment of the present invention will now be described through reference to FIGS. 28 to 32.

Figure 28:
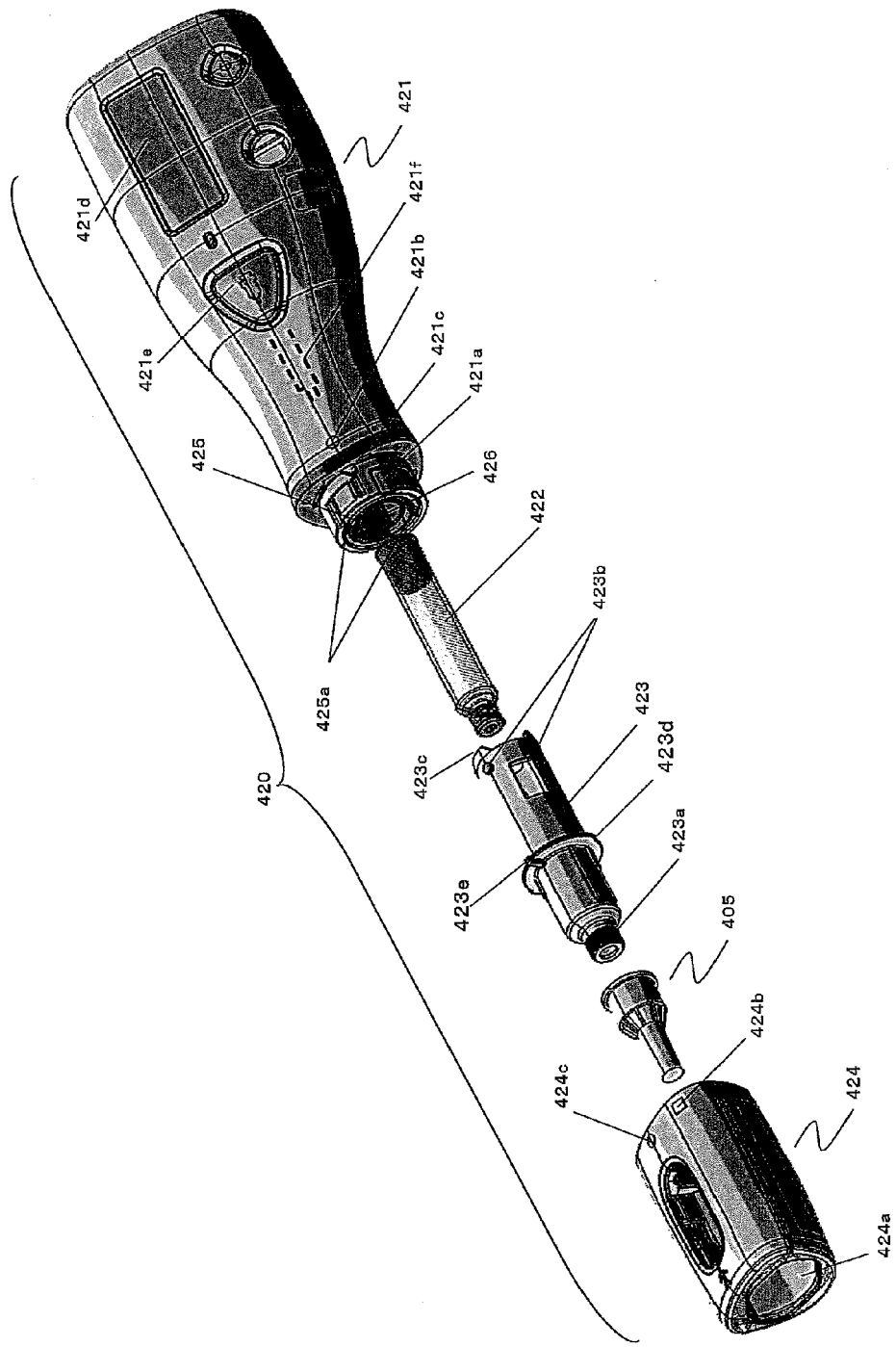
FIG. 28 is an exploded oblique view of the medication administering device in Embodiment 7 of the present invention.
Figure 29:
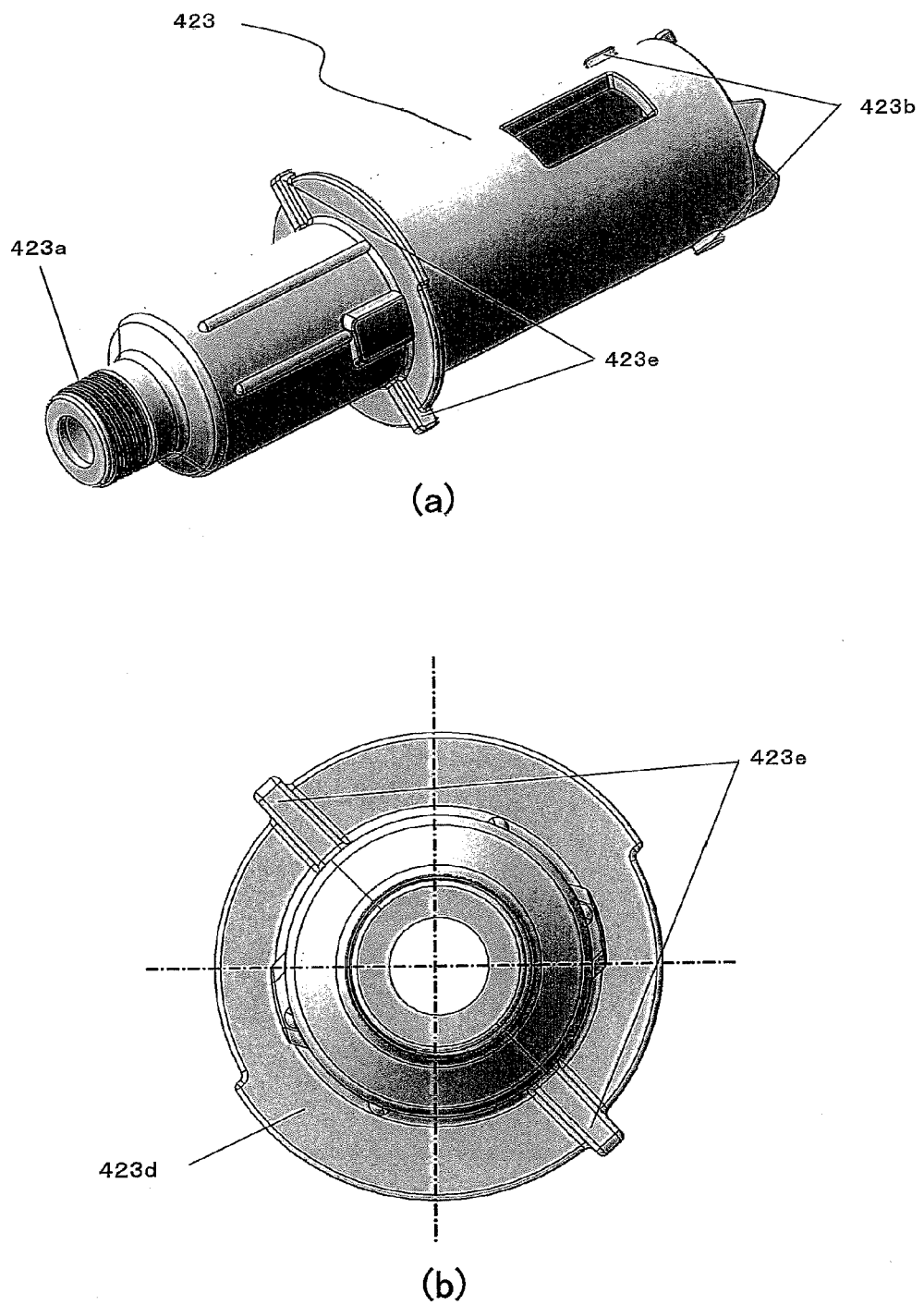
FIG. 29(a) is an oblique view of the syringe cover as seen from the side where the needle is mounted in Embodiment 7.
FIG. 29(b) is a front view of the syringe cover as seen from the side where the needle is mounted in Embodiment 7.
Figure 30:
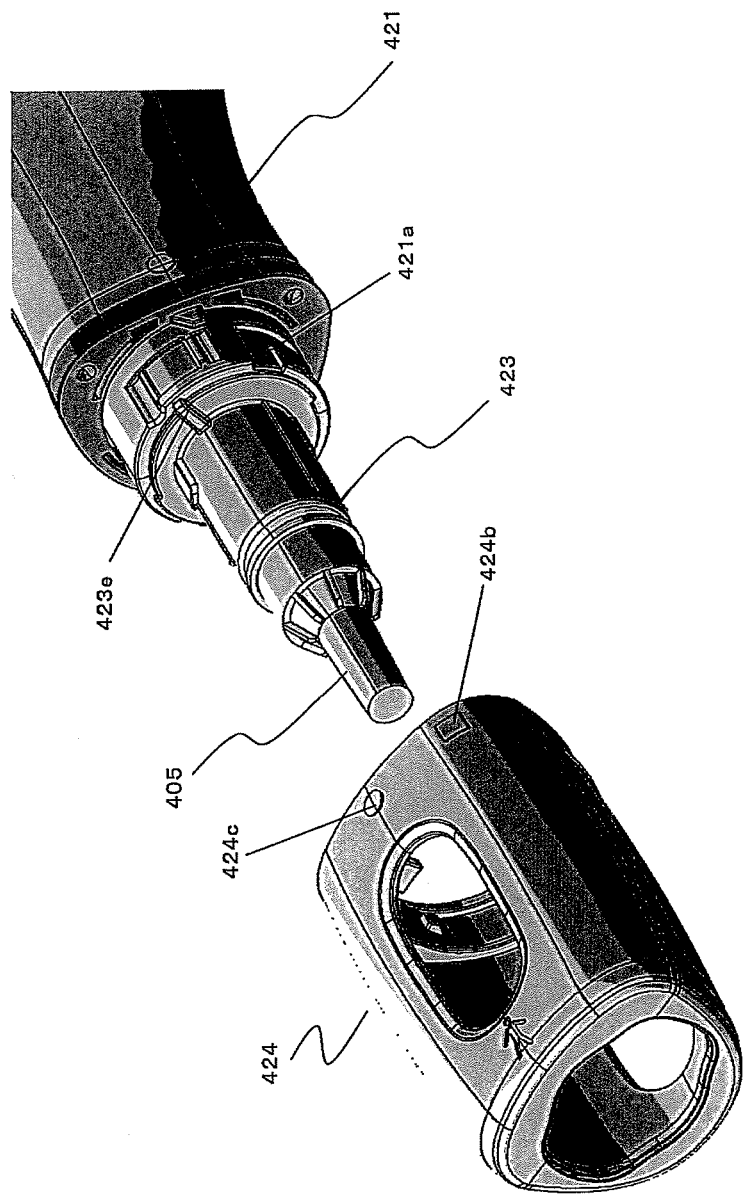
FIG. 30 is an oblique view in which the distal end cap is mounted to the main body.
Figure 31:
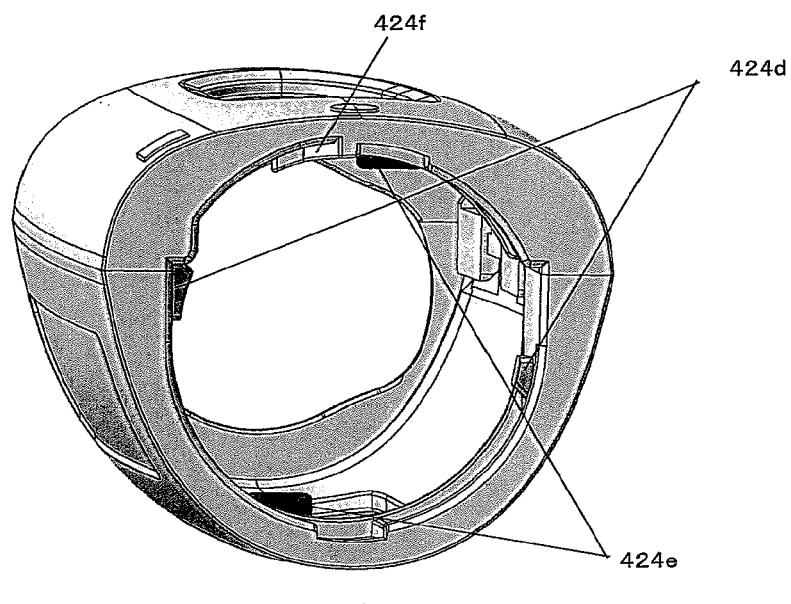
FIG. 31(a) is an oblique view of the distal end cap as seen from the side where it is mounted to the main body.
FIG. 31(b) is a front view of the distal end cap as seen from the side where it is mounted to the main body.
Figure 31:
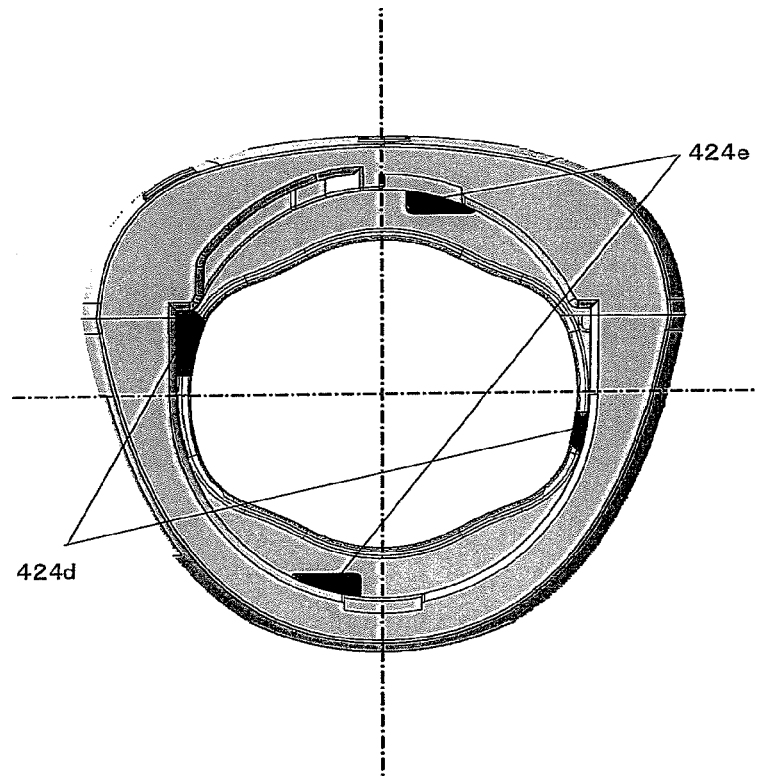
Figure 32:
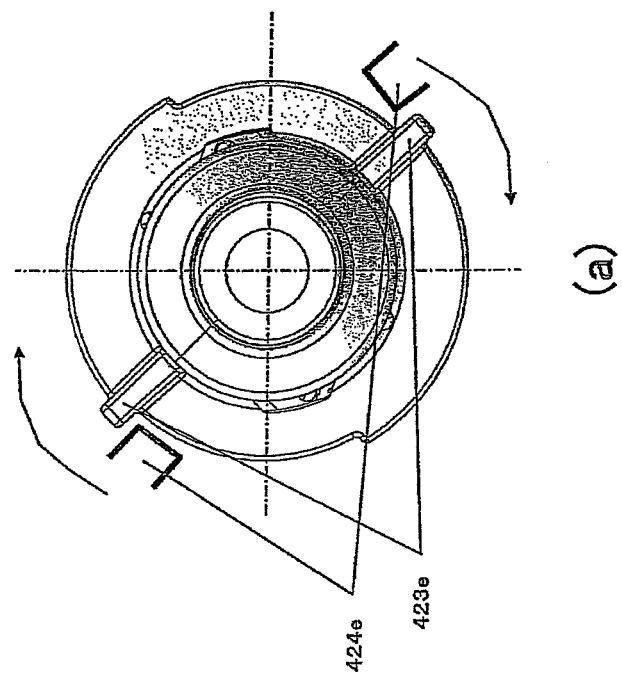
FIG. 32(a) is a front view of a state in which the mounting of the syringe cover has not been completed, as seen from the side where the needle is mounted.
FIG. 32(b) is a front view of a state in which the mounting of the syringe cover has been completed, as seen from the side where the needle is mounted.
Figure 32:
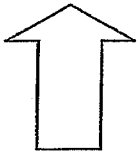
Figure 32:
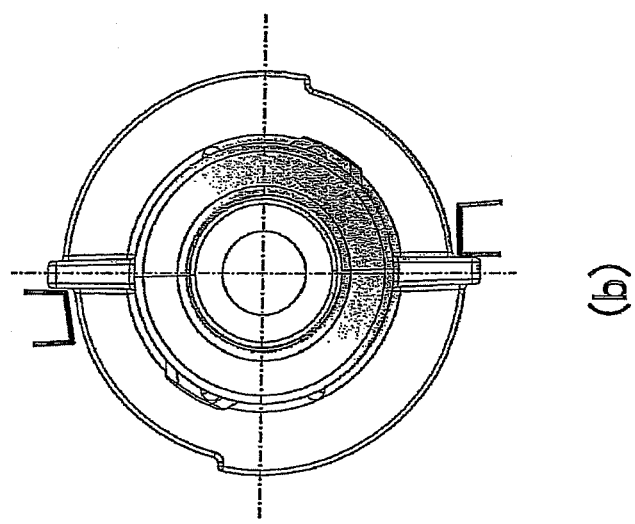

As shown in FIG. 28, the medication administering device 420 of this embodiment comprises a main body 421, a preparation syringe 422, a syringe cover 423, a needle portion 405, and a distal end cap 424.

The main body 421 is the main portion of the medication administering device 420, and performs control of the administration operation, displays information, and is operated by an administration start button, and as such has the main functions of medication administration and operation.

Also, the main body 421 has distal end cap guide grooves 421$a$, a positioning mark 421$b$, a distal end cap detecting lever 421$c$, a display component 421$d$, a medication administering button 421$e$, and a syringe cover detecting lever 421$f$. The distal end cap guide grooves 421$a$ guide the distal end cap 424 during attachment and removal. The positioning mark 421$b$ serves as a benchmark that allows the distal end cap 424 to be attached and removed more easily. The distal end cap detecting lever 421$c$ detects that the distal end cap 424 has been properly mounted. The display component 421$d$ displays the remaining battery charge and various kinds of information necessary for operation. The medication administering button 421$e$ is pressed when medication is administered after the completion of preparation for the administration of medication. The syringe cover detecting lever 421$f$ detects that the syringe cover 423 has been mounted.

The main body 421 further has a syringe holder 426 that allows the insertion of the preparation syringe 422 containing a preparation, and an inner case 425 that can slide together with the syringe holder 426 during medication administration. The inner case 425 has the preparation syringe 422 built into it and has syringe cover fastening grooves 425$a$ that allow the attachment and removal of the syringe cover 423 mounted to the main body 421 of the medication administering device 420.

The syringe cover 423 is made from a transparent member, so the built-in preparation syringe 422 can be checked. Also, the syringe cover 423 has at one end a needle mounting portion 423a that allows the attachment and removal of the needle portion 405, and has fastening dowels 423b and cover detecting lever pressing portions 423c that engage with the syringe cover fastening grooves 425a provided to the inner case 425. As shown in FIGS. 29(a) and 29(b), the syringe cover 423 has a flange 423d that prevents the preparation or other such liquid from finding its way into the interior of the main body, and convex portions 423e having a shape that sticks out radially from the center.

The needle portion 405 is the portion of the injection needle that pierces the living body and administers the preparation syringe 422. Its configuration is the same as that described for the conventional example, and will therefore not be described again here.

The distal end cap 424 has a distal end opening 424a through which the needle is exposed and pierces the living body so that a medication solution can be injected, a mounting start positioning mark 424b that serves as a benchmark in attaching and removing the main body 421, and a mounting end positioning mark 424c. As shown in FIGS. 31(a) and 31(b), there are also distal end cap guide tabs 424d for attachment and removal utilizing the distal end cap guide grooves 421a of the main body 421, and engagement protrusions 424e that engage with the convex portions 423e that stick out radially from the syringe cover 423.

Also, a situation was described here in which two each of the fastening dowels 423b, the convex portions 423e, the distal end cap guide tabs 424d, and the engagement protrusions 424e were provided, but the present invention is not limited to this, and there may instead be one of each of these, or three or more of each.

<Operation of the Medication Administering Device 420>

The medication administering device 420 pertaining to an embodiment of the present invention will now be described through reference to FIGS. 28 to 32.

First, the preparation syringe 422 is inserted into the syringe holder 426 provided on the main body 421 side of the medication administering device 420, and the syringe cover 423 is mounted. At this point the fastening dowels 423b are aligned with the syringe cover fastening grooves 425a provided to the inner case 425, and inserted straight in, after which the components are rotated and fixed. When the syringe cover 423 has been properly mounted, the cover detecting lever pressing portions 423c press on the syringe cover detecting lever 421f, which turns on a switch (not shown) on the main body 421. However, if the syringe cover 423 is not in the right position, the switch will remain off as the next operation is performed.

Then, the needle portion 405 is rotated and attached to the needle mounting portion 423a at one end of the syringe cover 423, and the distal end cap 424 is mounted. After straight-ahead insertion so that the mounting start positioning mark 424b and the positioning mark 421b on the main body 421 line up, the component is rotated clockwise up to the mounting end positioning mark 424c. At this point the distal end cap guide tabs 424d are guided by and fixed in the distal end cap guide grooves 421a of the main body 421. If the distal end cap 424 has been properly mounted, then a cap detecting lever pressing portion 424f presses on the distal end cap detecting lever 421c, and a switch (not shown) on the main body 421 is turned on. As shown in FIGS. 32(a) and 32(b), even if the syringe cover 423 is not completely mounted at this point, the engagement protrusions 424e will engage with the convex portions 423e that stick out radially, allowing integral rotation, and the syringe cover 423 is mounted.

After this, the user grasps the protective cap of the needle portion 405 and removes it through the distal end opening 424a, and then grasps and removes the needle cap of the needle portion 405.

FIG. 32(a) shows a state in which the syringe cover 423 has not been completely mounted, while FIG. 32(b) shows a state in which the syringe cover 423 has been completely mounted. Both FIGS. 32(a) and 32(b) are views in the preparation syringe 422 direction from the distal end opening 424a side. The above procedure completes the pre-preparation for administering a medication solution.

As discussed above, with this embodiment, the medication administering device 420 to which the preparation syringe 422 containing a preparation is mounted and which is able to administer to a living body or the like comprises the cylindrical syringe cover 423 that supports the preparation syringe 422, the inner case 425 that guides and removably fits together with the syringe cover 423, and the distal end cap 424 that guides and removably fits together with the main body 421. The convex portions 423e that stick out radially and are provided to the syringe cover 423 engage with the engagement protrusions 424e provided to the distal end cap 424, and the syringe cover 423 can also be rotated by rotation of the distal end cap 424.

Consequently, even if the syringe cover 423 is not completely mounted, as long as the distal end cap 424 is properly mounted, the syringe cover 423 will be forcibly mounted. Thus, a medication administering device can be provided with which there is far less improper mounting, reliability is improved, and the device is easier to use.

Also, with the medication administering device of this embodiment, the preparation syringe is supported on the inner peripheral face side of the syringe cover, the inner case guides the outer peripheral face side of the syringe cover, and the distal end cap guides part of the outer peripheral face of the main body.

With the medication administering device of this embodiment, the syringe cover supporting the preparation syringe is pushed in while being rotated with respect to the inner case, and the mounting of the syringe cover is complete at the point when the inner case reaches the locked position.

With the medication administering device of this embodiment, the main body has guide grooves and indicators that show the mounting position. The distal end cap has an indicator showing the mounting start position and an indicator showing the mounting end position, and is provided with guide tabs. The indicator showing the mounting position of the main body, and the indicator showing the mounting start position of the distal end cap are aligned and the distal end cap is pushed in, and the guide grooves and the guide tabs are aligned, after which the components are pushed in while being rotated, which mounts the distal end cap on the main body.

With the medication administering device of this embodiment, the syringe cover is formed from a transparent or semi-transparent member so that the preparation syringe inside can be checked visually, and has a flange that prevents liquid from coming in from the outside.

With the medication administering device of this embodiment, the syringe cover has a plurality of fastening dowels disposed at regular intervals or at symmetrical positions around the center axis of the syringe cover.

With the medication administering device of this embodiment, the syringe cover has a plurality of convex portions disposed at regular intervals or at symmetrical positions around the center axis of the syringe cover.

With the medication administering device of this embodiment, the positional relation between the convex portions and the fastening dowels of the syringe cover is that they are disposed at the same angular positions, or at positions other than the same angles, around the center axis of the syringe cover.

With the medication administering device of the present invention, since the distal end cap is mounted to the main body, when it is pushed in while being rotated, the engagement protrusions provided to the distal end cap press on the convex portions provided to the syringe cover located on the inside. Consequently, simultaneously with the conclusion of the mounting of the distal end cap to the main body, the syringe cover is also pushed and rotated by the engagement protrusions and its mounting to the inner case is concluded.

With the medication administering device of the present invention, even if the mounting of the front portion (the syringe cover, etc.) is incomplete, as long as the distal end cap is mounted properly, the front portion will be forcibly mounted, so a medication administering device can be provided with which improper mounting is far less likely to occur, reliability is improved, and the device is easier to operate.

REFERENCE EXAMPLE 3

A medication administering device with which the puncture needle was inserted electrically into a living body and then removed after the injection of the preparation has been put to practical use in the past as a medication administering device for easily administering a preparation to a living body.

Figure 33:
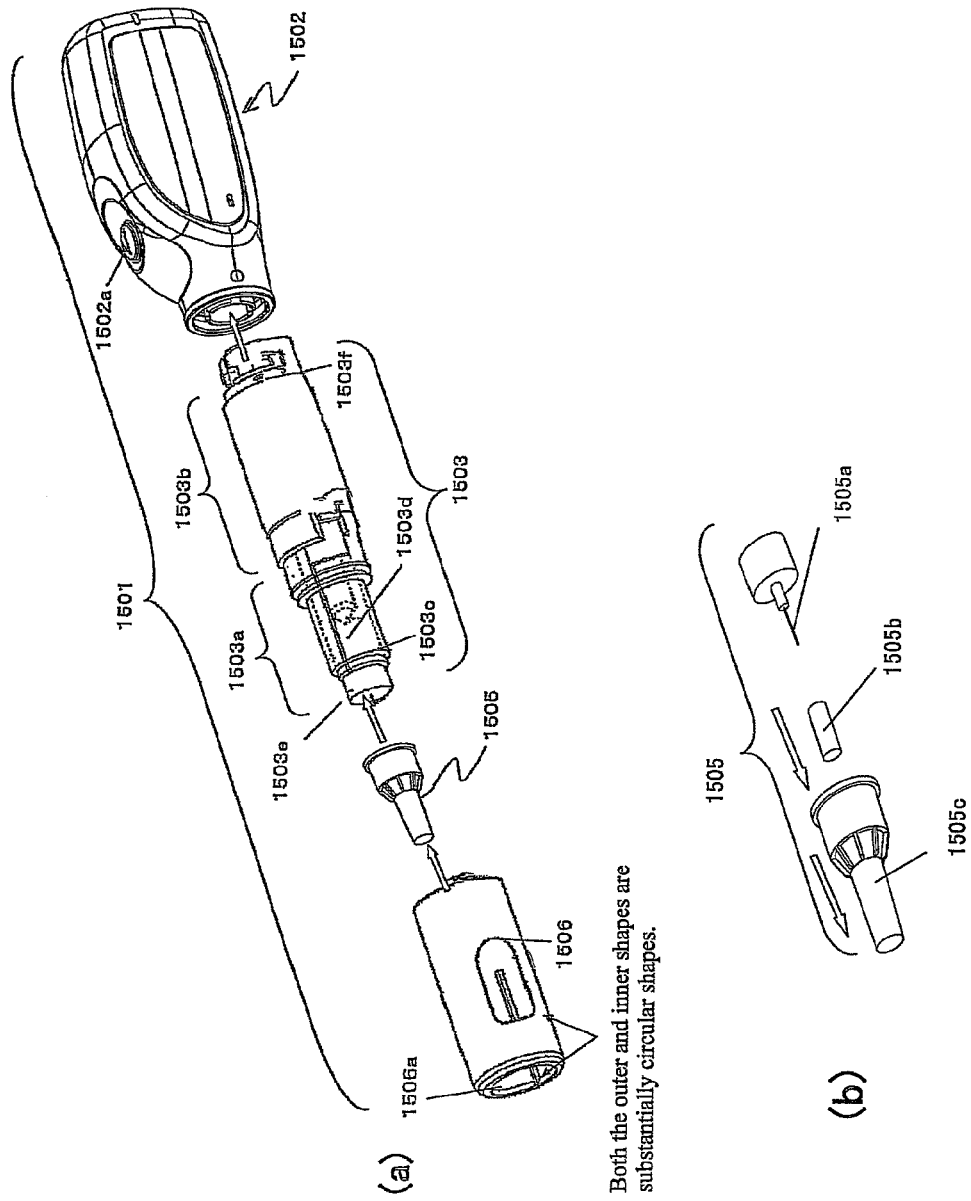
FIG. 33(a) is an exploded oblique view of a conventional medication administering device.
FIG. 33(b) is a diagram of the constituent parts of the needle portion used in the medication administering device.

Specifically, as shown in FIG. 33(a), when a medication administering device 1501 such as this is used, the user first docks a syringe 1503a and a front case component 1503b. In between these two, a slidably constituted front component 1503 is mounted to a main body 1502. At this point, a fastening groove 1503f formed at one end of the front case component 1503b allows the attachment and removal of the front case component 1503b and the main body 1502. The members constituted by the syringe 1503a and the members constituted by the main body 1502 are then linked, and the syringe 1503a is able to slide (not shown).

After this, a needle portion 1505 is rotated and attached to a needle mounting portion 1503e, and a front cap 1506 is inserted straight into the front case component 1503b. The outer shape of the front cap 1506 is substantially cylindrical, and a front cap opening 1506a formed at the distal end thereof is also substantially cylindrical.

Here, the needle portion 1505 has a needle 1505a, a needle cap 1505b, and a protective cap 1505c. The needle mounting portion 1503e is provided at one end of a preparation syringe 1503d mounted in a housing 1503c that constitutes the syringe 1503a (see Japanese Laid-Open Patent Application 2005-287676, for example).

However, with the conventional medication administering device 1501, the user first aligns the fastening groove 1503f of the front component 1503, which holds the preparation syringe 1503d, with a tab (not shown) provided to the main body 1502. Then, the needle portion 1505 for injecting the preparation is attached to the needle mounting portion 1503e, and the front cap 1506 is mounted to the front case 1503b. After this, the protective cap 1505c and the needle cap 1505b are removed through a front cap opening 1506a.

After these operations have been performed, when a medication administering button 1502a on the main body 1502 is pressed, the syringe 1503a slides, and the injection needle 1505a is exposed by a few millimeters from the distal end of the front cap 1506. After the required amount of preparation has been injected, the syringe 1503a slides back to its original position, the needle 1505a returns from the distal end of the front cap 1506, and the series of preparation administration operations is concluded.

With the conventional usage method discussed above, as shown in FIG. 33(b), a problem was that it was difficult for the user to remove the needle cap 1505b and the protective cap 1505c of the needle portion 1505 mounted to the medication administering device 1501.

This prevents the needle portion 1505 having the needle 1505a from being safely exposed to the outside, so the position of the needle 1505a always has to be on the inside of the front cap 1506 and other such members, and there is no practical way to lengthen the protective cap 1505c of the needle 1505a and other such components. Also, although operation can be facilitated by making the opening in the front cap 1506 larger, the front cap 1506 also serves to come into contact with the skin and keep the puncture distance constant. Accordingly, if this opening is made larger, then how much the skin rises up will vary greatly depending on how the front cap 1506 is placed against the skin. As a result, there is variance in the puncture distance, which can cause more discomfort during puncture, so the opening of the front cap 1506 cannot actually be made any larger.

Also, when the front component 1503 or the needle portion 1505 is mounted, a problem has been that the front cap 1506 tends to roll when it is removed from the medication administering device 1501.

The following embodiment solves the above problems, and it is an object thereof to provide a medication administering device that injects a preparation into a living body, wherein the protective cap of the needle and the needle cap are easy to take off, the front cap does not readily roll by itself, and the device is easier to handle.

(Embodiment 8)

A medication administering device 520 pertaining to yet another embodiment of the present invention will now be described through reference to FIGS. 34 to 37.

Figure 34:
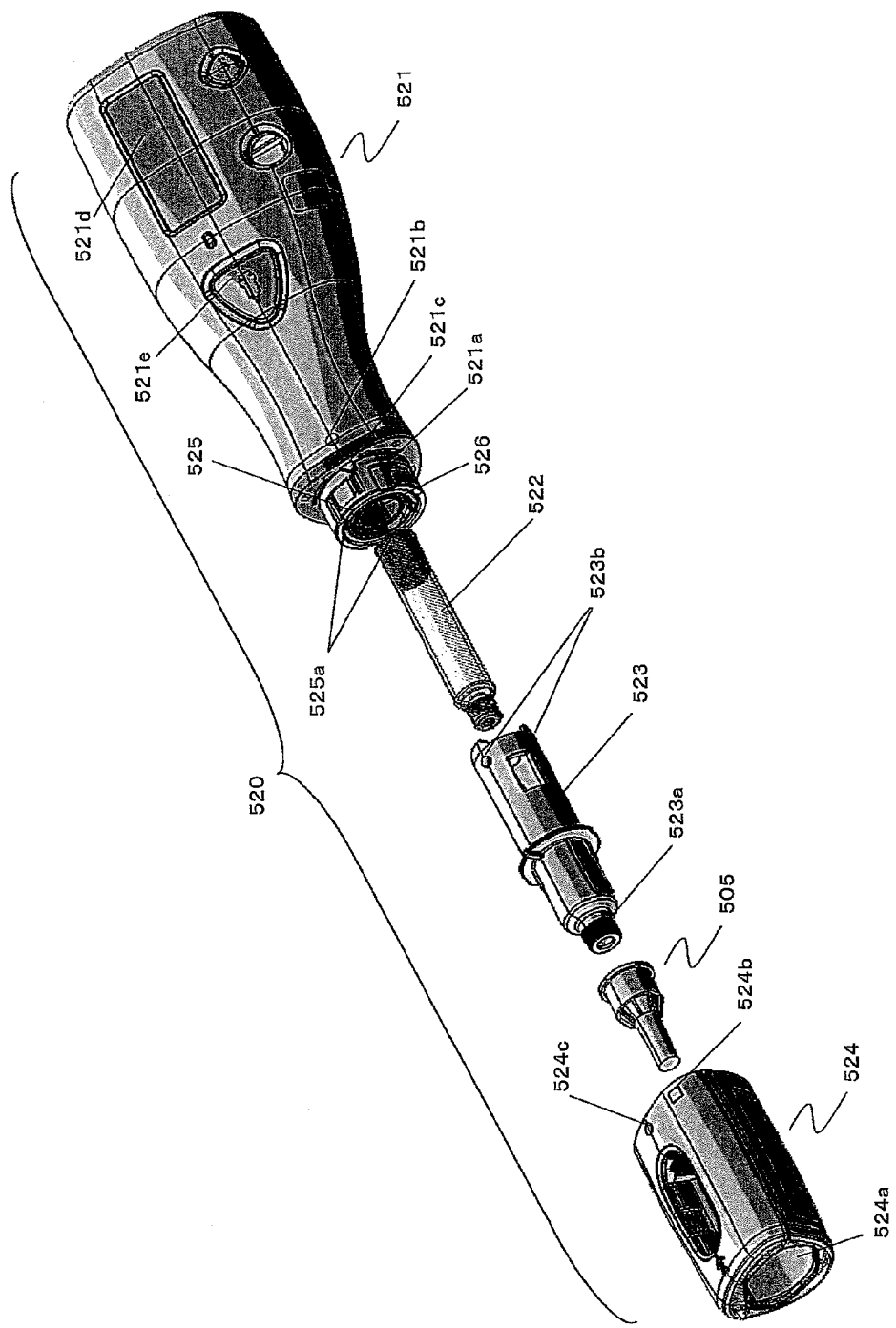
FIG. 34 is an exploded oblique view of the medication administering device in Embodiment 8 of the present invention.
Figure 35:
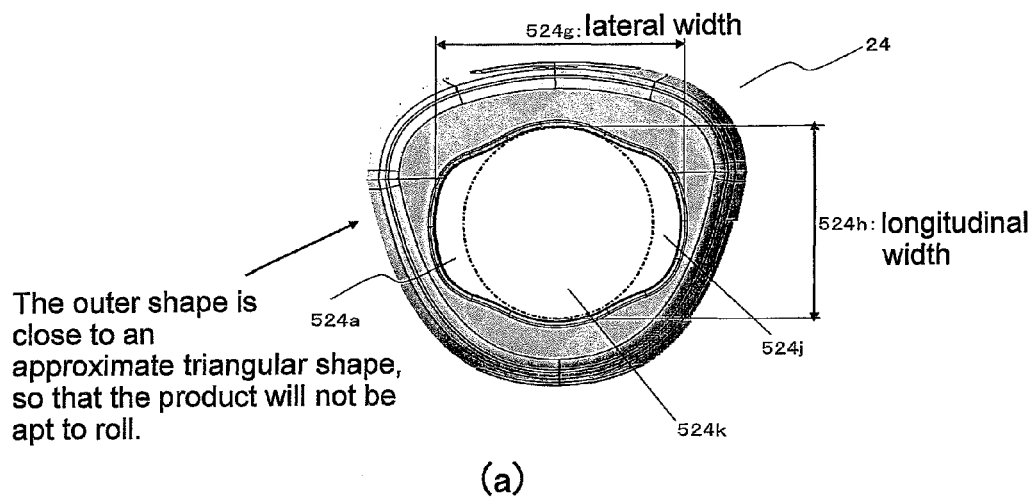
FIG. 35(a) is a front view of the distal end cap as seen from the side placed against the skin.
FIG. 35(b) is an oblique view of the distal end cap as seen from the side placed against the skin.
Figure 35:
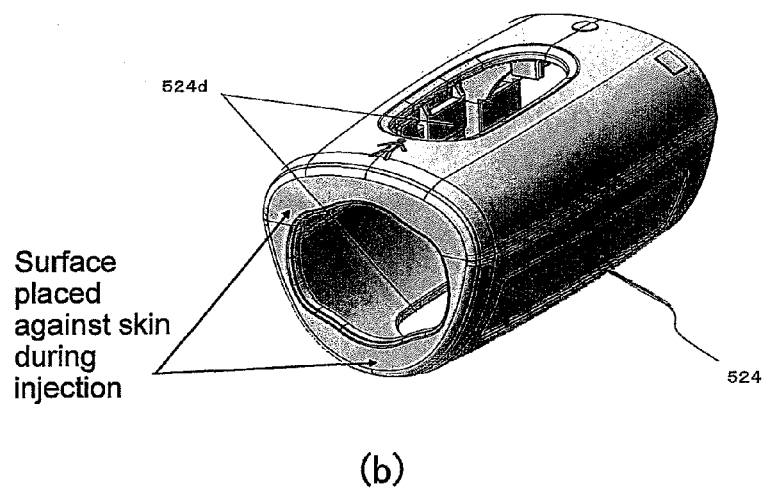

As shown in FIG. 34, the medication administering device 520 of this embodiment is constituted by a main body 521, a preparation syringe 522, a syringe cover 523, a needle portion 505, and a distal end cap 524.

The main body 521 has distal end cap guide grooves 521a, a positioning mark 521b, a distal end cap detecting lever 521c, a display component 521d, and a medication administering button 521e. The distal end cap guide grooves 521a guide the distal end cap 524 during attachment and removal. The positioning mark 521b serves as a benchmark that allows the distal end cap 524 to be attached and removed more easily. The distal end cap detecting lever 521c detects that the distal end cap 524 has been properly mounted. The display component 521d displays the remaining battery charge and various kinds of information necessary for operation. The medication administering button 521e is pressed when medication is administered after the completion of preparation for the administration of medication.

The main body 521 further has an inner case 525 that can slide during medication administration and that allows the insertion of the preparation syringe 522 into which the medication has been sealed. The inner case 525 has the preparation syringe 522 built into it and has syringe cover fastening grooves 525a that allow the attachment and removal of the syringe cover 523 mounted to the main body 521 of the medication administering device 520.

The syringe cover 523 is made from a transparent member, so the built-in preparation syringe 522 can be checked. Also, the syringe cover 523 has at one end a needle mounting portion 523a that allows the attachment and removal of the needle portion 505. The syringe cover 523 further has fastening dowels 523b that engage with the syringe cover fastening grooves 525a provided to the inner case 525.

The needle portion 505 is constituted the same as in the conventional example, and so will not be described here.

The distal end cap 524 has a substantially cylindrical shape with an opening at both ends. The inner peripheral face thereof is structured so as to allow movement of the syringe cover to which are mounted the preparation syringe 522 and a needle 505a used for injection. Also, the distal end cap is the portion that comes into contact with the skin (the living body) during injection of the preparation, and also has the function of maintaining a constant distance between the needle 505a and the skin, and thereby maintaining a constant injection depth. This reduces pain during injection.

The distal end cap 524 has a distal end opening 524a through which the needle 505a protrudes and pierces the skin so that a medication solution can be injected, a mounting start positioning mark 524b that serves as a benchmark in attaching and removing the main body 521, and a mounting end positioning mark 524c. As shown in FIG. 35(a), the distal end opening 524a has a shape that combines a substantially circular shape 524k and a slot shape 524j, with the longitudinal width 524h being different from the lateral width 524g. This results in a place where the protective cap and the needle cap 505b are easy to grasp, which reduces the effort on the part of the user when these are removed. Furthermore, this prevents the skin from rising up too much, and prevents the attendant increase in discomfort caused by piercing. One possibility is a shape in which the diameter of the circular shape is about 20 mm, and the longer portion is about 25 mm, but there are other possibilities as well.

The shape of the distal end opening 524a may also be a simple elliptical shape, or a combination of a circular shape and an elliptical shape. However, in terms of ease of work and reliability, it is best for the inner face shape to have undulating curves at a plurality of places, as shown in FIG. 35(a).

Furthermore, as shown in FIG. 35(b), whether or not the preparation syringe 522 is inside, what type it is, the amount of preparation, and so forth can be checked visually through the transparent syringe cover 523, without having to remove the 524 from the medication administering device 520, because of a preparation check window 524d. The check window 524d is provided here, but the window 524d portion may instead be cut out or formed from a transparent member, or the entire distal end cap 524 may be formed from a transparent or semi-transparent member.

The cross sectional shape of the distal end cap 524 is a shape that is substantially close to being triangular, which is a stable shape that is resistant to rolling when the cap is placed on a table or the like by itself. The cross sectional shape is not limited to being triangular, however, and may instead be elliptical or polyhedral.

Figure 36:
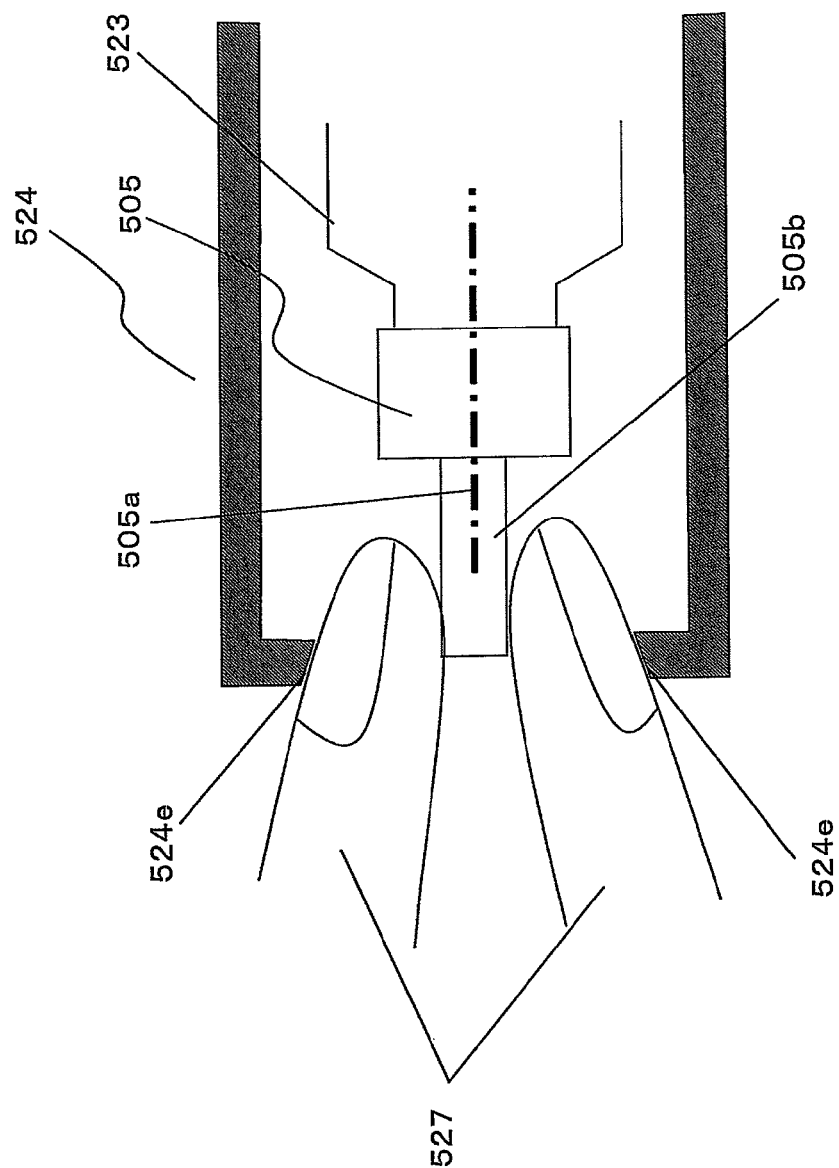
FIG. 36 is a cross section of the above-mentioned distal end cap.

FIG. 36 is a cross section showing how the needle cap 505b of the needle portion 505 inside the distal end cap 524 is taken out.

As shown in FIG. 36, the inner portion of the distal end opening 524a of the distal end cap 524 has a taper shape 524e. The needle cap 505b is grasped by fingers 527 from the slot shape 524j side (see FIG. 35(a)) of the distal end opening 524a, and when the fingers 527 are rotated, the needle cap 505b is lifted in the removal direction, which means that the operation is easy. That is, just by turning the fingers 527 grasping the needle cap 505b, the fingers 527 are pushed by the outer part of the distal end cap 524 along the internal shape of the distal end opening 524a. Accordingly, the operation of pulling out the needle cap 505b is also performed, and the needle cap 505b can be removed with ease. This is extremely effective in practical terms.

In particular, when handling a sharp object such as the needle 505a and the portion around it, the ease of operation of the present invention, in which no extra force is necessary, is extremely effective from the standpoint of safety.

Figure 37:
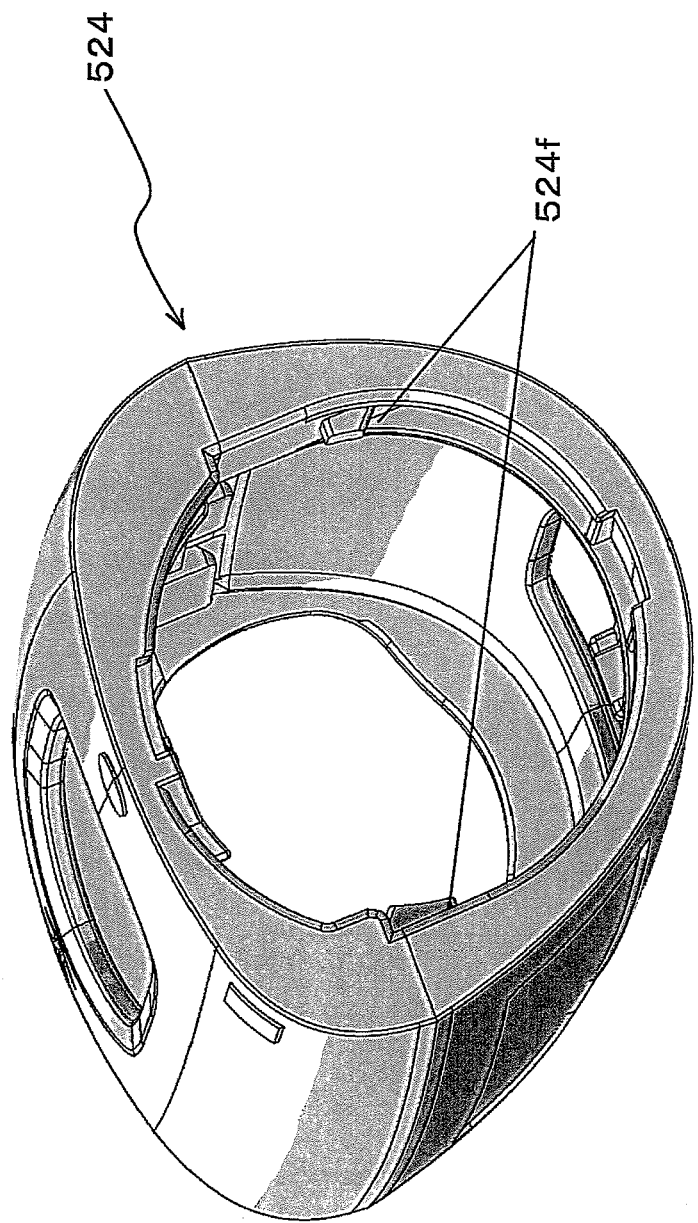
FIG. 37 is an oblique view of the distal end cap as seen from the side where it is mounted to the main body of the medication administering device.

FIG. 37 is an oblique view of the outside of the distal end cap 524 as seen from the opposite side from the distal end opening 524a. Guide tabs 524f engage with the distal end cap guide grooves 521a provided to the main body 521 of the medication administering device 520, and are used in the operation of mounting and removing the distal end cap 524 to and from the medication administering device 520.

<Method for Operating the Medication Administering Device 520>

The operation of the medication administering device 520 in this embodiment will now be described through reference to FIGS. 34 to 37.

First, the preparation syringe 522 is inserted into the inner case 525 provided to the main body 521 of the medication administering device 520, and the syringe cover 523 is mounted. At this point the fastening dowel 523b of the syringe cover 523 is aligned with the syringe cover fastening groove 525a provided to the inner case 525, and the syringe cover 523 is inserted straight in and then rotated and fixed.

Next, the needle portion 505 is rotated and attached to the needle mounting portion 523a at one end of the syringe cover 523, after which the distal end cap 524 is mounted. After straight-ahead insertion so that the mounting start positioning mark 524b and the positioning mark 521b on the main body 521 line up, the component is rotated clockwise up to the mounting end positioning mark 524c. At this point the guide tabs 524f are guided by and fixed in the distal end cap guide grooves 521a.

After this, the user grasps the protective cap 505c and removes it through the distal end opening 524a, and then grasps and removes the needle cap 505b from the needle portion 505. At this point the fingers 527 are inserted through the slot shape 524j portion in a direction in which it is easy for the fingers 527 to fit, and the fingers 527 are either pulled straight out or rotated. Consequently, the fingers 527 move to the circular shape 524k portion with a smaller radius, and the needle cap 505b is pulled off along the taper shape 524e.

The above procedure completes the pre-preparation for administering a medication solution.

As discussed above, with this embodiment, the medication administering device 520 to which the preparation syringe 522 containing a preparation is mounted and which is able to administer to a living body or the like comprises the syringe cover 523 to and from which the needle 505a that administers the preparation can be attached and removed, and with which the preparation syringe 522 is mounted to the main body 521, and the distal end cap 524 that covers the syringe cover 523, removably fits together with the main body 521, and has the distal end opening 524a that comes into contact with the living body. The distal end opening 524a of the distal end cap 524 has a shape that combines a portion where fingers can easily fit and a portion that prevents the flesh from rising up when the cap is pressed against the skin, and also has a shape that resists rolling when the cap is set down by itself.

Consequently, the operation of removing the needle cap 505b and the protective cap 505c of the needle 505a constituting the needle portion 505 is easier, and a medication administering device can be provided that is safe and easy to handle.

(Embodiment 9)

The configuration of a distal end cap 624 used in the medication administering device pertaining to this embodiment will be described through reference to FIG. 38.

Figure 38:
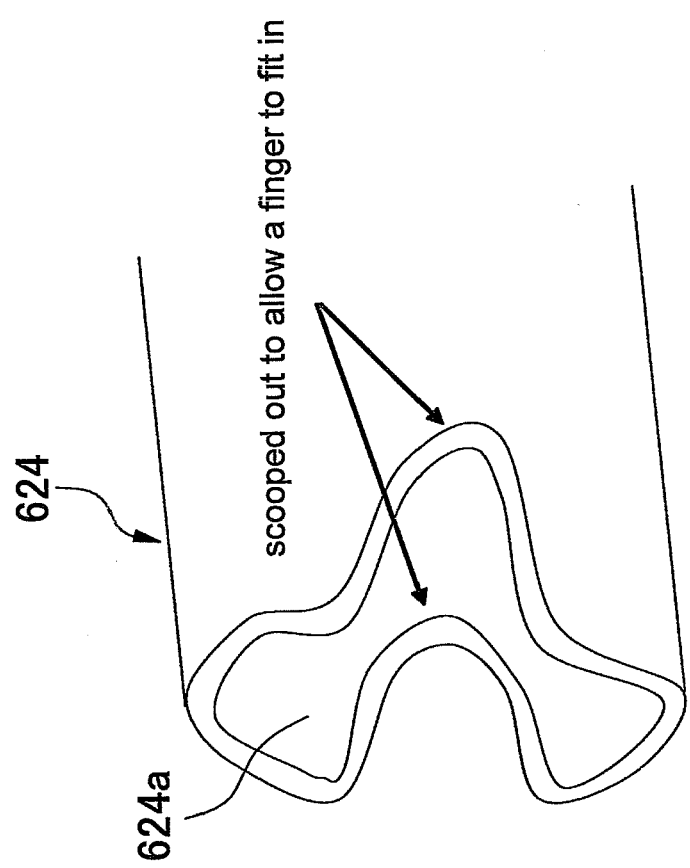
FIG. 38 is an oblique view of the distal end cap in Embodiment 9 of the present invention.

In FIG. 38, the shape of the distal end opening 624a of the distal end cap 624 is changed in the height direction, and the distal end portion has a scooped out shape that makes it easier for fingers to fit in. The depth of the scooped out portion is from 5 to 15 mm, and a diameter of about 20 mm is aimed at for the opening, but the present invention is not limited to these values.

Up until the mounting of the distal end cap 624, everything is the same as described in Embodiment 8 above, and will not be described again.

Upon completion of the mounting of the distal end cap 624, the protective cap 505c of the needle portion 505 is grasped and removed through the distal end opening 624a. Then, when the needle cap 505b is grasped and removed from the needle portion 505, if the fingers are inserted and rotated from the places with the scooped out shape in the distal end opening 624a, the needle cap 505b will move in the distal end direction and can be simply removed.

(Embodiment 10)

The configuration of the distal end cap 724 used in the medication administering device pertaining to this embodiment will be described through reference to FIG. 39.

Figure 39:
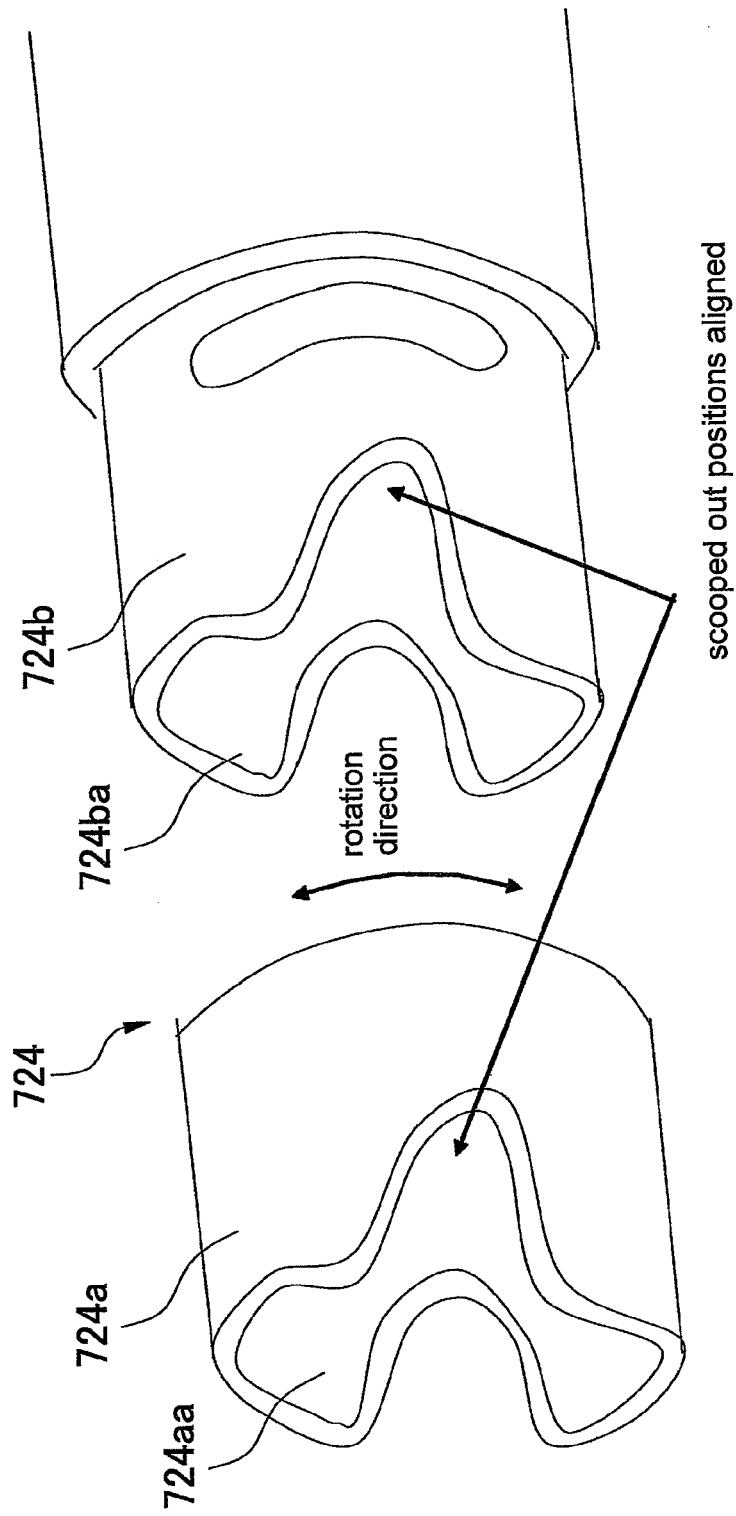
FIG. 39 is an oblique view of the distal end cap in Embodiment 10 of the present invention.

FIG. 39 shows a configuration in which the distal end component has a dual structure in which a rotatable separate piece 724a is provided at the distal end of the distal end cap 724, and the phases are different between the two kinds of members in which the shape of the distal end opening 724aa is changed in the height direction. The fixed-side piece 724b and the separate piece 724a of the distal end cap 724 have three-dimensionally similar shapes.

Upon completion of the mounting of the distal end cap 724, the protective cap 505c (see FIG. 36) is grasped and removed through the distal end opening 724aa. Then, when the needle cap 505b (see FIG. 36) is grasped and removed from the needle portion 505 (see FIG. 36), the rotatable separate piece 724a is rotated so that it matches the scooped out shape of the distal end opening 724ba of the fixed-side piece 724b. This creates a place where the fingers easily fit in, and allows the protective cap 505c and the needle cap 505b to be simply removed.

Next, the rotatable separate piece 724a is rotated so that it does not match the scooped out shape of the fixed-side piece 724b, constituting a flat face. After this, if a medication solution is to be administered with the medication administering device, the skin is suitably kept from rising up, which prevents any increase in discomfort upon puncture.

(Embodiment 11)

The configuration of the distal end cap 824 used in the medication administering device pertaining to this embodiment will be described through reference to FIG. 40.

Figure 40:
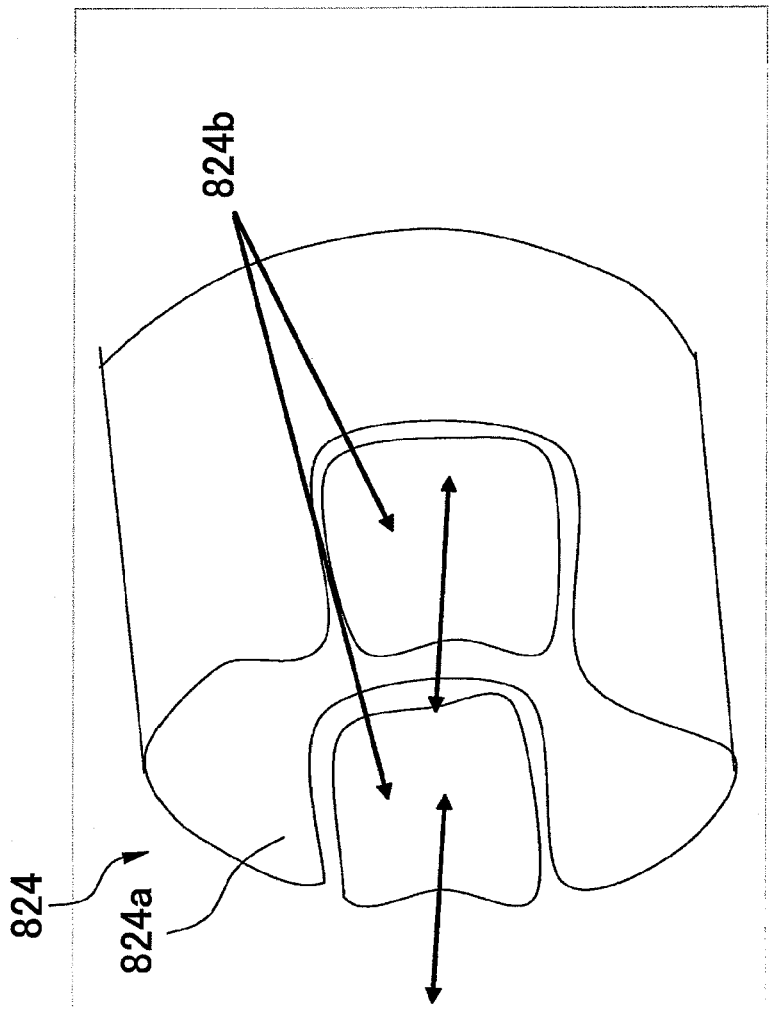
FIG. 40 is an oblique view of the distal end cap in Embodiment 11 of the present invention.

FIG. 40 shows a configuration in which an opening and closing separate piece 824b is provided to the distal end of the distal end cap 824. The position of the distal end cap 824 is usually limited by a spring and a stopper, which are held at the same diameter as the external shape of the distal end cap 824, and only widen outward when fingers are inserted.

Upon completion of the mounting of the distal end cap 824, the protective cap 505c (see FIG. 36) is grasped and removed through the distal end opening 824a. Then, when the needle cap 505b (see FIG. 36) is grasped and removed from the needle portion 505 (see FIG. 36), the fingers are worked from the place where the opening and closing separate piece is provided.

This allows the separate piece 824b to be opened and simply removed. Also, if the fingers are moved away, the opening and closing separate piece 824b goes back to the stopper position on its own under the biasing of the elastic body. Since the medication solution is administered by the medication administering device in this state, the skin is suitably kept from rising up, which prevents any increase in discomfort upon puncture.

Also, the medication administering device of this embodiment is the medication administering device pertaining the embodiments given above, wherein, when the distal end cap is mounted to the main body, the distal end of the needle mounted to the syringe cover is short enough not to be exposed to the outside from the distal end cap.

Consequently, even after the mounting of the needle, the needle is covered by the distal end cap, there is no danger such as accidental needle puncture since the needle does not stick out, so operation is safer.

The medication administering device of this embodiment is the medication administering device pertaining the embodiments given above, wherein the distal end cap has a portion that comes into contact with the living body, so it is molded from a plastic material that is gentle on the living body.

This makes the device safer and more pleasant to use.

With the medication administering device of the present invention, a medication administering device can be provided with which the protective cap of the needle and the needle cap are easy to take off, the distal end cap does not readily roll by itself, and the device is easier to handle.

The medication administering device pertaining to the present invention has the effect of allowing a syringe cover to be securely and easily placed in the device, so it is particularly useful as a medication administering device used for self-injection by seniors, children, and handicapped users, or for injection to a patient by a family member, etc.

The invention claimed is:

1. A medication administering device for having a preparation syringe containing a preparation mounted thereto, and for administering the preparation to a living body, said device comprising:

a substantially cylindrical syringe cover having an outer peripheral face, a substantially cylindrical inner peripheral face side and being configured to support the preparation syringe on the substantially cylindrical inner peripheral face side of the substantially cylindrical syringe cover;

a substantially cylindrical piston configured to press on a rear end of the preparation syringe;

a piston case surrounding the substantially cylindrical piston, being configured to guide the outer peripheral face of the substantially cylindrical syringe cover in the direction of the substantially cylindrical piston on the substantially cylindrical inner peripheral face side, and being configured to be mounted in a state in which the syringe cover is removable;

a housing having an inner peripheral surface surrounding the piston case, and being configured to move the piston case forward in a puncture direction along the inner peripheral surface along with the syringe cover when the rear end of the preparation syringe is pushed by the piston; and a syringe cover detector configured to detect if the syringe cover has been mounted to the piston case.

2. The medication administering device according to claim 1,
wherein the syringe cover has a fastening tab that protrudes from the outer peripheral face, and
the piston case has a fastening groove on an inner peripheral face side of the piston case where the syringe cover is mounted, and is configured to mate with the fastening tab.

3. The medication administering device according to claim 1,
further comprising a syringe detector configured to detect if the preparation syringe has been installed in the piston case.

4. The medication administering device according to claim 1,
wherein the syringe cover detector includes a syringe cover detecting lever, a syringe cover detecting lever spring configured to bias the syringe cover detecting lever in one direction, and a syringe cover detecting switch configured to be switched on and off by the syringe cover detecting lever.

5. The medication administering device according to claim 1,
further comprising a syringe identifier configured to identify an identification piece provided on the preparation syringe.

6. The medication administering device according to claim 1,
wherein the syringe cover further includes an inclined part configured to contact a shoulder of a distal end outer peripheral part on a side where the preparation syringe is to be inserted.

7. The medication administering device according to claim 1,
wherein the syringe cover has a substantially cylindrical shape.

8. The medication administering device according to claim 1,
wherein all or part of the syringe cover is transparent or semitransparent.

9. The medication administering device according to claim 1,
wherein the syringe cover has a preparation syringe mounting prong configured to support an end of the preparation syringe during mounting of the preparation syringe.

10. The medication administering device according to claim 1,
wherein the syringe cover has a syringe mounting arm configured to support an end of the preparation syringe during mounting of the preparation syringe, and configured to release the support of the end of the preparation syringe when use of the preparation syringe is finished.

11. A medication administering device for having a preparation syringe containing a preparation mounted thereto, and for administering the preparation to a living body, said device comprising:
a substantially cylindrical syringe cover having a cylindrical inner peripheral face side, an inner peripheral face, and being configured to support the preparation syringe on the inner peripheral face side of the substantially cylindrical syringe cover;
a piston configured to press on a rear end of the preparation syringe;
a syringe holder configured to surround the piston at a specific position, being configured to guide an outer peripheral face of the preparation syringe in the direction of the piston on the cylindrical inner peripheral face side, and having an outer peripheral face configured to be removably fitted together with the inner peripheral face of the syringe cover, and
a housing covering the syringe cover, the piston, and the syringe holder inside so that the preparation syringe is capable of being fixed in the inner peripheral face side of the syringe cover, and the syringe cover is disposed on the outer peripheral side of the syringe holder in a when the syringe cover is attached to the syringe holder having the preparation syringe,
wherein the syringe holder has an inner peripheral face side and an outer periphery limiting protrusion on the inner peripheral face side, the outer periphery limiting protrusion being configured to limit the position of the outer peripheral face of the preparation syringe, and the syringe holder is configured to form a space between the outer peripheral surface of the preparation syringe and the inner peripheral surface of the syringe cover, the space being formed so that the syringe holder is inserted from the rear end of the preparation syringe.

12. The medication administering device according to claim 11,
wherein the syringe holder has a tapered part on the inner peripheral face side, the tapered part widening toward an opening in which the preparation syringe is capable of being inserted.

13. The medication administering device according to claim 11,
wherein the syringe holder has an inner periphery limiting protrusion configured to limit the position of an inner peripheral face of the preparation syringe, at a portion that is capable of contacting the rear end of the preparation syringe.

14. The medication administering device according to claim 11,
where the syringe holder has a syringe detector configured to detect that the preparation syringe has been mounted.

15. The medication administering device according to claim 11,
wherein the syringe holder has a syringe identifier configured to identify an identification piece provided on the preparation syringe.

16. The medication administering device according to claim 11,
further comprising a substantially cylindrical piston case surrounding the piston and the syringe holder,
wherein the syringe cover has a fastening tab protruding from the outer peripheral face, and
the substantially cylindrical piston case has a fastening groove configured to mate with the fastening tab, on an inner peripheral face side.

17. The medication administering device according to claim 11, wherein the housing surrounds the syringe holder.

* * * * *